United States Patent
Leumann et al.

(10) Patent No.: US 9,249,178 B2
(45) Date of Patent: Feb. 2, 2016

(54) TRICYCLIC NUCLEOSIDES AND OLIGOMERIC COMPOUNDS PREPARED THEREFROM

(71) Applicant: UNIVERSITÄT BERN, Bern (CH)

(72) Inventors: Christian Leumann, Bern (CH); Branislav Dugovic, Bern (CH); Jory Liétard, Bern (CH)

(*) Notice: Subject to any disclaimer, the term of this patent is extended or adjusted under 35 U.S.C. 154(b) by 0 days.

(21) Appl. No.: 14/385,050

(22) PCT Filed: Mar. 15, 2013

(86) PCT No.: PCT/EP2013/055498
§ 371 (c)(1),
(2) Date: Sep. 12, 2014

(87) PCT Pub. No.: WO2013/135900
PCT Pub. Date: Sep. 19, 2013

(65) Prior Publication Data
US 2015/0141637 A1    May 21, 2015

(30) Foreign Application Priority Data
Mar. 15, 2012  (EP) .................................. 12159716

(51) Int. Cl.
| | | |
|---|---|---|
| C07H 21/02 | (2006.01) |
| C07H 21/04 | (2006.01) |
| C07H 21/00 | (2006.01) |
| C07H 19/16 | (2006.01) |
| C07H 19/04 | (2006.01) |
| C07H 19/02 | (2006.01) |
| C07H 19/06 | (2006.01) |

(52) U.S. Cl.
CPC ................ *C07H 21/00* (2013.01); *C07H 19/02* (2013.01); *C07H 19/04* (2013.01); *C07H 19/06* (2013.01); *C07H 19/16* (2013.01)

(58) Field of Classification Search
None
See application file for complete search history.

(56) References Cited

PUBLICATIONS

Renneberg et al. JACS (2002), vol. 124, pp. 5993-6002.*
Lietard, J., et al., "Synthesis, Pairing, and Cellular Uptake Properties of C(6')- Functionalized Tricyclo-DNA," *Journal of Organic Chemistry 77*: 4566-4577 (2012), ACS Publications.
Renneberg, D., et al., "Watson—Crick Base-Pairing Properties of Tricyclo-DNA," *J. Am. Chem. Soc. 124*: 5993-6002 (2002) American Chemical Society.

* cited by examiner

*Primary Examiner* — Patrick Lewis
(74) *Attorney, Agent, or Firm* — Fanelli Haag PLLC

(57) ABSTRACT

The present invention provides novel tricyclic nucleosides and oligomeric compounds prepared therefrom. Incorporation of one or more of the tricyclic nucleosides into an oligomeric compound is expected to enhance one or more properties of the oligomeric compound. Such oligomeric compounds can also be included in double stranded compositions. In certain embodiments, the oligomeric compounds provided herein are expected to hybridize to a portion of a target RNA resulting in loss of normal function of the target RNA.

23 Claims, No Drawings

TRICYCLIC NUCLEOSIDES AND OLIGOMERIC COMPOUNDS PREPARED THEREFROM

SEQUENCE LISTING

The instant application contains a Sequence Listing which has been submitted electronically in ASCII format and is hereby incorporated by reference in its entirety. Said ASCII copy, created on Jan. 12, 2014, is named P3268PC00_corrected_SeqList.txt and is 20,480 bytes i size.

FIELD OF THE INVENTION

The present invention relates to tricyclic alkyl-substituted nucleosides described by the general Formula I and oligomeric compounds prepared therefrom.

BACKGROUND OF THE INVENTION

Antisense technology is an effective means for reducing the expression of specific gene products and can therefore be useful in therapeutic, diagnostic, and research applications. Generally, the principle behind antisense technology is that an antisense compound (a sequence of oligonucleotides or analogues thereof) hybridizes to a target nucleic acid and modulates gene expression activities or function, such as transcription and/or translation. Regardless of the specific mechanism, its sequence-specificity makes antisense compounds attractive as tools for target validation and gene functionalization, as well as therapeutics to selectively modulate the expression of genes involved in the pathogenesis of diseases.

Chemically modified nucleosides are routinely incorporated into antisense compounds to enhance its properties, such as nuclease resistance, pharmacokinetics or affinity for a target RNA.

Chemical modifications have improved the potency and efficacy of antisense compounds, improving their potential for oral delivery or subcutaneous administration, or decreasing their potential for side effects. Chemical modifications increasing potency of antisense compounds allow administration of lower doses, which reduces the potential for toxicity. Modifications increasing the resistance to degradation result in slower clearance from the body, allowing for less frequent dosing. The synthesis of tricyclic nucleosides (Steffens et al., Helvetica Chimica Acta, 1997, 80, 2426-2439) and their incorporation into oligomeric compounds has been reported in the literature (Steffens et al., J. Am. Chem. Soc., 1997, 119, 11548-11549; Steffens et al., J. Am. Chem. Soc., 1999, 121, 3249-3255; Renneberg et al., J. Am. Chem. Soc., 2002, 124, 5993-6002; Scheidegger et al., Chem. Eur. J., 2006, 12, 8014-8023). Fully modified tricyclic oligonucleotides were shown to be more stable against nucleolytic degradation in fetal calf serum compared to unmodified oligodeoxynucleotides and to produce biological antisense effects in cellular assays, such as splice restoration of mutant β-globin (Renneberg et al., Nucleic Acids Res. 2002, 30, 2751-2757); or exon skipping in cyclophilin A (Ittig et al., Nucleic Acids Research, 2004, 32, 346-353).

BRIEF SUMMARY OF THE INVENTION

Provided herein are tricyclic nucleosides having Formula I and oligomeric compounds prepared therefrom. More particularly, tricyclic nucleosides having Formula I are useful for incorporation at one or more positions of an oligomeric compound. In certain embodiments, the oligomeric compounds provided herein are characterized by one or more enhanced properties such as nuclease stability, cell permeability, bioavailability or toxicity. In certain embodiments, the oligomeric compounds as provided herein hybridize to a portion of a target RNA resulting in loss of normal function of the target RNA. The oligomeric compounds provided herein are also useful as primers and probes in diagnostic applications. In certain embodiments, oligomers comprising tricyclic nucleosides provided herein show significantly improved—compared to unmodified DNA or RNA oligomers—cellar uptake independent of transfection reagents such as liposomes. In certain embodiments, oligomers comprising tricyclic nucleosides provided herein show significantly increased—compared to unmodified DNA or RNA oligomers—thermal stability (duplex melting point).

The variables are defined individually in further detail herein. It is to be understood that the tricyclic nucleosides having Formula I and the oligomeric compounds provided herein include all combinations of the embodiments disclosed and variables defined herein.

According to a first aspect of the invention, a tricyclic nucleoside is provided that is described by the general Formula I:

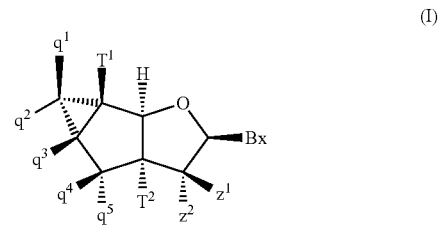

wherein:
Bx is a heterocyclic base moiety;
one of $T^1$ and $T^2$ is hydroxyl (—OH) or a protected hydroxyl and the other of $T^1$ and $T^2$ is a phosphate or a reactive phosphorus group, with $T^1$ optionally being a solid support for oligonucleotide synthesis;
$q^1$ and $q^2$ are each, independently, H, F or Cl,
at least one of $q^3$, $q^4$ and $q^5$ is, independently, a group described by a general formula -$A^1$-$X_h$-$A^2$-$Y_n$, wherein
$A^1$ is a $C_k$-alkyl, $C_k$-alkenyl or $C_k$-alkynyl, with k being an integer selected from the range of 0 to 20,
$X_h$ is —C(═O)—, —C(═O)O—, —C(═O)NR—, —O—, —S—, —NR—, —C(═O)R, —C(═O)OR, —C(═O)NR$_2$—, —OR, —SR or —NR$_2$, with each R being selected independently from H, methyl, ethyl, propyl, butyl, acetyl and 2-hydroxyethyl, and h is 0 or 1,
$A^2$ is a $C_i$-alkyl, $C_i$-alkenyl or $C_i$-alkynyl, with i being an integer selected from the range of 0 to 20,
Y is a substituent group attached to any carbon atom on $A^1$ and/or $A^2$, selected from —F, —Cl, —Br, ═O, —OR, —SR, —NR$_2$, —NR$_3$+, NHC(═NH)NH$_2$, —CN, —NC, —NCO, —NCS, —SCN, —COR, —CO$_2$R, CONR$_2$, —R, with each R being selected independently from H, methyl, ethyl, propyl, butyl, acetyl and 2-hydroxyethyl, and n is 0, 1, 2, 3, 4, 5 or 6, wherein k+i equals at least 1,
and wherein any —OR, —SR, —NR$_2$, —CO$_2$R, CONR$_2$ for which R is H may optionally be protected by a protecting group used in solid phase oligonucleotide chemistry, the other ones of $q^3$, $q^4$ and $q^5$ are, independently, H, F or Cl, one of $z^1$ and $z^2$ is H and the other of $z^1$ and $z^2$ is H, —OH, F, Cl, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—N$(CH_3)_2$, $OCH_2C$(=O)—N(H)$CH_3$, $OCH_2C$(=O)—N(H)—$(CH_2)_2$—N$(CH_3)_2$ or $OCH_2$—N(H)—C(=NH)$NH_2$.

One of ordinary skill in the art of organic chemistry understands that—concerning the selection of oxygen (=O) as a substituent group—the oxygen atom is attached via a double bond to any carbon atom on $A^1$ or $A^2$. A $C_k$-alkyl, $C_k$-alkenyl or $C_k$-alkynyl in the context of the present specification refers to an alkyl, alkenyl or alkynyl moiety, respectively, having k carbon atoms in a linear chain. The index i of $A^2$ is applied similarly. It is understood that embodiments for which k is 0, $A^1$ is not present, and for embodiments for which i is 0, $A^2$ is not present. If n substituent groups are present, these can be present both on $A^1$ and $A^2$.

In some embodiments, Bx is a pyrimidine, substituted pyrimidine, purine or substituted purine. In some embodiments, Bx is selected from uracil, thymine, cytosine, 5-methylcytosine, adenine and guanine. In some embodiments, Bx is an aromatic heterocyclic moiety capable of forming base pairs when incorporated into DNA or RNA oligomers in lieu of the bases uracil, thymine, cytosine, 5-methylcytosine, adenine and guanine.

In some embodiments, $T^1$ is hydroxyl or protected hydroxyl, and $T^2$ is a reactive phosphorus group selected from an H-phosphonate or a phosphoramidite. In some embodiments, $T^1$ is a triphosphate group and $T^2$ is OH. In some embodiments, $T^1$ is 4,4'-dimethoxytrityl and $T^2$ is diisopropylcyanoethoxy phosphoramidite. In some embodiments, $T^1$ is a controlled pore glass surface. According to certain embodiments of this embodiment, $T^1$ is a long chain alkylamine controlled pore glass surface or similar solid phase support used in oligonucleotide solid phase synthesis, to which a 3'-O-succinylated nucleoside is linked via an amide function.

In some embodiments, one of $z^1$ and $z^2$ is F, $OCH_3$ or $O(CH_2)_2$—$OCH_3$. In some embodiments, one of $z^1$ and $z^2$ is F. In some embodiments, one of $z^1$ and $z^2$ is F and the other one is H. In some embodiments, $z^1$ and $z^2$ are each H. In some embodiments, $z^1$ and $z^2$ are each F. In some embodiments, $z^1$ and $z^2$ are each H.

In some embodiments, $q^1$ and $q^2$ are H. In some embodiments, one of $q^1$ and $q^2$ is F and the other one is H.

In certain embodiments, the tricyclic nucleoside carries in position $q^3$, $q^4$ or $q^5$ one substituent having 3 to about 18 carbon atoms, optionally with a cationic group on the chain. Such substituents are useful for incorporation into oligonucleotides that, as a function of the alkyl substituent chain length and substitution and the number of such modified nucleotides, provide improved transport of the oligonucleotide in the body, and improved cellular uptake. Without wishing to be bound by theory, the inventors hypothesize that the observed behavior of such modified oligonucleotides may at least partially be explained by self-aggregation of the oligonucleotides by hydrophobic interaction.

EMBODIMENTS A

In some embodiments, the substituent is a $C_3$ to $C_{16}$ alkyl moiety, i.e. k is 3, 4, 5, 6, 7, 8, 9, 10, 11, 12, 13, 14, 15 or 16, h is 0, i is 0 and n is 1, 2, or 3. In a subgroup thereof, a $C_3$ to $C_{16}$ alkyl moiety is in position $q^3$; $q^4$ and $q^5$ are H, and optionally, one of $q^1$ and $q^2$ is H and the other one is F or Cl, or both of $q^1$ and $q^2$ are H. In another subgroup thereof, a $C_3$ to $C_{16}$ alkyl moiety having 1-6 substituents is in position $q^4$ or $q^5$, the other one of $q^4$ and $q^5$, and $q^3$, are H, and optionally, one of $q^1$ and $q^2$ is H and the other one is F or Cl, or both of $q^1$ and $q^2$ are H.

EMBODIMENTS B

In some embodiments, the substituent is an acetic acid $C_3$ to $C_{16}$ amide or ester, i.e. k is 1, h is 1 and X is COO—, CONH— or CONR—, i is 3, 4, 5, 6, 7, 8, 9, 10, 11, 12, 13, 14, 15 or 16 and n is 1, 2, or 3. In a subgroup thereof, an acetic acid $C_3$ to $C_{16}$ amide or ester is in position $q^3$; $q^4$ and $q^5$ are H, and optionally, one of $q^1$ and $q^2$ is H and the other one is F or Cl, or both of $q^1$ and $q^2$ are H. In another subgroup thereof, an acetic acid $C_3$ to $C_{16}$ amide or ester is in position $q^4$ or $q^5$, the other one of $q^4$ and $q^5$, and $q^3$, are H, and optionally, one of $q^1$ and $q^2$ is H and the other one is F or Cl, or both of $q^1$ and $q^2$ are H.

EMBODIMENTS C

In some embodiments, the substituent is an $C_3$ to $C_{16}$ alkoxy moiety, i.e. k is 0, h is 1 and X is —O—, i is 3, 4, 5, 6, 7, 8, 9, 10, 11, 12, 13, 14, 15 or 16 and n is 1, 2, or 3. In a subgroup thereof, a $C_3$ to $C_{16}$ alkoxy moiety is in position $q^3$; $q^4$ and $q^5$ are H, and optionally, one of $q^1$ and $q^2$ is H and the other one is F or Cl, or both of $q^1$ and $q^2$ are H. In another subgroup thereof, a $C_3$ to $C_{16}$ alkoxy moiety is in position $q^4$ or $q^5$, the other one of $q^4$ and $q^5$, and $q^3$, are H, and optionally, one of $q^1$ and $q^2$ is H and the other one is F or Cl, or both of $q^1$ and $q^2$ are H.

EMBODIMENTS D

In some embodiments, $q^3$ is the group described by the general formula -$A^1$-$X_h$-$A^2$-$Y_n$, k and i independently are 0, 1, 2, 3, 4, 5, 6, 7, 8, 9, 10, 11, 12, 13, 14 or 15 and the sum of k and i is at least 3 and no more than 17, h is 1 and X is selected from COO—, CONH—, CONR—, —O—, and CO, and n is 0, 1, 2, or 3. In a subgroup thereof, $q^4$ and $q^5$ are H, and optionally, one of $q^1$ and $q^2$ is H and the other one is F or Cl, or both of $q^1$ and $q^2$ are H.

EMBODIMENTS E

In some embodiments, either of $q^4$ or $q^5$ is the group described by the general formula -$A^1$-$X_h$-$A^2$-$Y_n$, k and i independently are 0, 1, 2, 3, 4, 5, 6, 7, 8, 9, 10, 11, 12, 13, 14 or 15 and the sum of k and i is at least 3 and no more than 17, h is 1 and X is selected from COO—, CONH, CONR—, —O—, and CO, and n is 0, 1, 2, or 3. In a subgroup thereof, the other one of $q^4$ and $q^5$, and $q^3$, are H, and optionally, one of $q^1$ and $q^2$ is H and the other one is F or Cl, or both of $q^1$ and $q^2$ are H.

Further defining the embodiments of group A, B, C, D and E, a subgroup of any one of these embodiments is characterized by n being 1 and the substituent Y being a cationic substituent selected from $NH_2$, NHR, $NR_2$, $NR_3^+$ and NHC(=NH)$NH_2$ (guanidyl), with R having the meaning outlined above. In some of these embodiments, the cationic substituent is positioned on the ω-position (terminal C) of the alkyl chain being farthest away from the nucleoside ring ($A^1$ in embodiments of group A, $A^2$ in embodiments of group B, C, D and E).

EMBODIMENTS F

In some embodiments, the tricyclic nucleoside carries one substituent that is defined by the following parameters: k is 0, h is 1, $X_h$ is —O—, —C(=O)O— or —C(=O)NH— and $A^2$-Y is $(CH_2)_mCH_3$, $(CH_2)_mCH_2OH$, $(CH_2)_mCH_2NH_2$, or $(CH_2)_mCH_2NHC(=NH)NH_2$, with m being 1, 2, 3, 4, 5, 6, 7, 8, 9, 10, 11, 12, 13, 14, 15 or 16. In a subgroup thereof, the substituent as defined in the previous sentence is in position $q^3$; in another subgroup, the substituent as defined in the previous sentence is in position $q^4$ or $q^5$. All other positions of $q^3$, $q^4$ and $q^5$ are H. Optionally, one of $q^1$ and $q^2$ is H and the other one is F or Cl, or both of $q^1$ and $q^2$ are H.

Embodiments having a single substituent $q^3$: In some embodiments, $q^1$, $q^2$, $q^4$ and $q^5$ are H and $q^3$ is a group described by the general formula $-A^1-X_h-A^2-Y_n$. Specific examples are given as groups G, H, I and J.

EMBODIMENTS G

In some embodiments, $q^3$ is
- $-(CH_2)_mCH_3$, $-(CH_2)_mCH_2OH$, $(CH_2)_mCH_2NH_2$, $(CH_2)_mCH_2NHC(=NH)NH_2$, or
- $-CO(CH_2)_mCH_3$, $CO-(CH_2)_mCH_2OH$, $CO(CH_2)_mCH_2NH_2$, or $CO(CH_2)_mCH_2NHC(=NH)NH_2$,
- $-COO(CH_2)_mCH_3$, $COO(CH_2)_mCH_2OH$, $COO(CH_2)_mCH_2NH_2$ or $COO(CH_2)_mCH_2NHC(=NH)NH_2$, or
- $-CONH(CH_2)_mCH_3$, $CONH(CH_2)_mCH_2OH$, $CONH(CH_2)_mCH_2NH_2$, or $CONH(CH_2)_mCH_2NHC(=NH)NH_2$, with m being 1, 2, 3, 4, 5, 6, 7, 8, 9, 10, 11, 12, 13, 14, 15 or 16. In a subgroup thereof, m is 3, 4, 5, 6, 7 or 8.

The length of the alkyl chain allows careful adjustment of delivery, bioavailability or permeability features of an oligonucleotide compound into which a nucleoside having this particular modification of $q^3$ is incorporated.

EMBODIMENTS H

In some embodiments, $q^3$ is a group described by the general formula $-A^1-X_h-A^2-Y_n$, wherein
- k of $A^1$ is 0, h is 1, $X_h$ is —O—, $A^2$ is $C_5$-alkyl and n of Y is 0, thus, $q^3$ is —O—$(CH_2)_4CH_3$, or
- k is 0, h is 1, $X_h$ is —C(=O)O—, $A^2$ is $C_6$-alkyl and n is 0, thus, $q^3$ is —C(=O)O—$(CH_2)_5CH_3$, or
- $A^1$ is $C_2$-alkyl, h is 1, $X_h$ is —C(=O)O—, $A^2$ is $C_6$-alkyl and n is 0, thus, $q^3$ is —$(CH_2)_2$—C(=O)O—$(CH_2)_5CH_3$, or
- k is 0, h is 1, $X_h$ is —C(=O)—, $A^2$ is $C_4$-alkyl and n is 0, thus, $q^3$ is —C(=O)—$(CH_2)_3CH_3$, or
- k is 0, h is 0, $A^2$ is $C_8$-alkyl, n is 1, and Y is —OH, wherein the substituent group —OH is attached to the co-carbon atom of the $C_8$-alkyl of $A^2$, thus, $q^3$ is —$(CH_2)_7CH_2OH$, or
- $A^1$ is —$CH_2$—, h is 1, $X_h$ is —$CO_2$H, wherein i and n are each 0, thus, $q^3$ is —$CH_2$—COOH, or
- $A^1$ is $CH_2$, h is 1, $X_h$ is —C(=O)O—, $A^2$ is $C_2$-alkyl and n is 0, thus, $q^3$ is —$CH_2$—C(=O)O—$CH_2CH_3$, or
- $A^1$ is $CH_2$, h is 1, $X_h$ is —$CONH_2$, i and n are each 0, thus, $q^3$ is —$CH_2$—$CONH_2$, or
- $A^1$ is $CH_2$, h is 1, $X_h$ is —C(=O)O—, $A^2$ is $C_{16}$-alkyl and n is 0, thus, $q^3$ is $CH_2$—C(=O)O—$(CH_2)_{15}CH_3$, or
- $A^1$ is $CH_2$, h is 1, $X_h$ is —C(=O)O—, $A^2$ is $C_3$-alkyl, n is 1 and $Y_n$ is —$NH_2$, wherein the substituent group —$NH_2$ is attached to the ω-carbon atom of the $C_3$-alkyl of $A^2$, thus, $q^3$ is $CH_2$—C(=O)O—$(CH_2)_3NH_2$, or
- $A^1$ is $CH_2$, h is 1, $X_h$ is —C(=O)NH—, $A^2$ is $C_3$-alkyl, n is 1 and $Y_n$ is —$NH_2$, wherein the substituent group —$NH_2$ is attached to the ω-carbon atom of the $C_3$-alkyl of $A^2$, thus, $q^3$ is $CH_2$—C(=O)NH—$(CH_2)_3NH_2$, or
- $A^1$ is $CH_2$, h is 1, $X_h$ is —C(=O)NH—, $A^2$ is $C_3$-alkyl, n is 1 and Y is —OH, wherein the substituent group —OH is attached to the ω-carbon atom of the $C_3$-alkyl of $A^2$, thus, $q^3$ is $CH_2$—C(=O)NH—$(CH_2)_3OH$.

EMBODIMENTS I

In some embodiments, $q^3$ is a group described by the general formula $-A^1-X_h-A^2-Y_n$, wherein $A^1$ is $CH_2$, h is 1, $X_h$ is —C(=O)OR, C(=O)$NR_2$, —C(=O)O— or —C(=O)NR—, with each R being selected independently from H, methyl, ethyl, propyl, butyl, acetyl and 2-hydroxyethyl in particular from H, methyl, ethyl, propyl and butyl. In a subgroup thereof, $z^1$, $z^2$, $q^1$, $q^2$, $q^4$ and $q^5$ are H. In a further subgroup thereof, $q^3$ is one of —$CH_2COOH$, —$CH_2C(=O)OCH_2CH_3$, —$CH_2CONH_2$, —$CH_2C(=O)O(CH_2)_3NH_2$, —$CH_2COO(CH_2)_{12-16}CH_3$, —$CH_2COO(CH_2)_{12-16}NH_2$, or —$CH_2C(=O)O$—$(CH_2)_3NH(Fmoc)$.

EMBODIMENTS J

In some embodiments, $q^3$ is one of —$CH_2COOH$, —$CH_2C(=O)OCH_2CH_3$, —$CH_2CONH_2$, —$CH_2C(=O)O(CH_2)_3NH_2$, —$CH_2COO(CH_2)_{12-16}CH_3$, or —$CH_2COO(CH_2)_{12-16}NH_2$, or —$CH_2C(=O)O$—$(CH_2)_3NH(Fmoc)$.

In a further subgroup thereof, the tricyclic nucleoside is selected from the group of a.

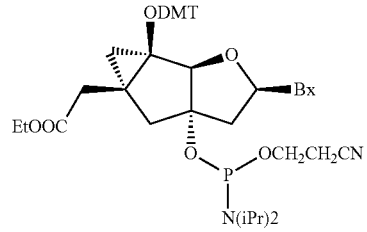

b.

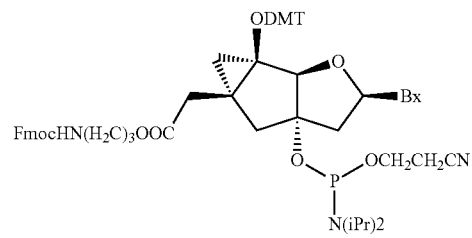

c.

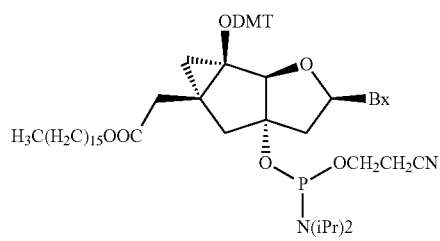

wherein Bx is selected from uracil, thymine, cytosine, 5-methylcytosine, adenine and guanine.

Also provided herein are nucleoside precursor compounds as exemplified by compound 8 of Example 1, compound 13 of Example 2 or compound 17 of Example 3, in particular:

d.

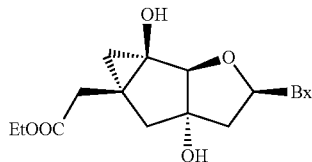

e.

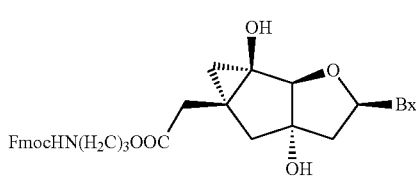

f.

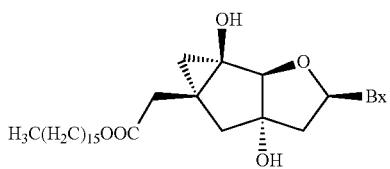

wherein Bx is selected from uracil, thymine, cytosine, 5-methylcytosine, adenine and guanine.

EMBODIMENTS K

In some embodiments, k is 0, h is 1, $X_h$ is —$CR_2$—, —C(=O)—, —C(=O)O—, —C(=O)NR—, —O—, —S—, —NR—, with each R being selected independently from H, methyl, ethyl, propyl and butyl, $A^2$ is a $C_i$-alkyl, $C_i$-alkenyl or $C_i$-alkynyl, with i being selected from any integer in the range of 1 to 20, Y is a substituent group attached to any carbon atom on $A^2$, selected from —F, —Cl, —Br, —OR, —SR, —$NR_2$, —CN, —NC, —NCO, —NCS, —SCN, —COR, —$CO_2R$, $CONR_2$, with each R being selected independently from H, methyl, ethyl, propyl, and butyl, and n is 0, 1, 2, 3, 4, 5 or 6.

EMBODIMENTS L

In some embodiments, k is 0, h is 1, $X_h$ is —$CR_2$—, —C(=O)—, —C(=O)O—, —C(=O)NR—, —O—, —S—, —NR—, with each R being selected independently from H, methyl, ethyl, propyl, and butyl, $A^2$ is a $C_i$-alkyl, $C_i$-alkenyl or $C_i$-alkynyl, with i being selected from any integer in the range of 1 to 20, Y is a substituent group attached to any carbon atom on $A^2$, selected from —F, —Cl, —Br, —OR, —SR, —$NR_2$, —CN, —NC, —NCO, —NCS, —SCN, —COR, —$CO_2R$, $CONR_2$, with each R being selected independently from H, methyl, ethyl, propyl, and butyl, and n is 0, 1, 2, 3, 4, 5 or 6, wherein if $z^1$, $z^2$, $q^1$, $q^2$, $q^4$ and $q^5$ are H, $q^3$ is one of —$CH_2COOH$, —$CH_2C(=O)OCH_2CH_3$, —$CH_2CONH_2$, —$CH_2C(=O)O(CH_2)_3NH_2$, —$CH_2COO(CH_2)_{12-16}CH_3$, —$CH_2COO(CH_2)_{12-16}NH_2$, or —$CH_2C(=O)O$—$(CH_2)_3NH(Fmoc)$, in particular one of —$CH_2C(=O)OCH_2CH_3$, —$CH_2C(=O)O(CH_2)_3NH_2$, —$CH_2COO(CH_2)_{15}CH_3$ or —$CH_2C(=O)O$—$(CH_2)_3NH(Fmoc)$.

EMBODIMENTS M

In some embodiments, $A^1$ is $CH_2$, h is 1, $X_h$ is —$CR_2$—, —C(=O)—, —C(=O)O—, —C(=O)NR—, —O—, —S—, —NR—, with each R being selected independently from H, methyl, ethyl, propyl and butyl, $A^2$ is a $C_i$-alkyl, $C_i$-alkenyl or $C_i$-alkynyl, with i being selected from any integer in the range of 1 to 20, Y is a substituent group attached to any carbon atom on $A^2$, selected from —F, —Cl, —Br, —OR, —SR, —$NR_2$, —CN, —NC, —NCO, —NCS, —SCN, —COR, —$CO_2R$, $CONR_2$, with each R being selected independently from H, methyl, ethyl, propyl, and butyl, and n is 0, 1, 2, 3, 4, 5 or 6.

EMBODIMENTS N

In some embodiments, $A^1$ is $CH_2$, h is 1, $X_h$ is —$CR_2$—, —C(=O)—, —C(=O)O—, —C(=O)NR—, —O—, —S—, —NR—, with each R being selected independently from H, methyl, ethyl, propyl, and butyl, $A^2$ is a $C_i$-alkyl, $C_i$-alkenyl or $C_i$-alkynyl, with i being selected from any integer in the range of 1 to 20, Y is a substituent group attached to any carbon atom on $A^2$, selected from —F, —Cl, —Br, —OR, —SR, —$NR_2$, —CN, —NC, —NCO, —NCS, —SCN, —COR, —$CO_2R$, $CONR_2$, with each R being selected independently from H, methyl, ethyl, propyl, and butyl, and n is 0, 1, 2, 3, 4, 5 or 6, wherein if $z^1$, $z^2$, $q^1$, $q^2$, $q^4$ and $q^5$ are H, $q^3$ is one of —$CH_2COOH$, —$CH_2C(=O)OCH_2CH_3$, —$CH_2CONH_2$, —$CH_2C(=O)O(CH_2)_3NH_2$, —$CH_2COO(CH_2)_{12-16}CH_3$, —$CH_2COO(CH_2)_{12-16}NH_2$, or —$CH_2C(=O)O$—$(CH_2)_3NH(Fmoc)$, in particular one of —$CH_2C(=O)OCH_2CH_3$, —$CH_2C(=O)O(CH_2)_3NH_2$, —$CH_2COO(CH_2)_{15}CH_3$ or —$CH_2C(=O)O$—$(CH_2)_3NH(Fmoc)$.

EMBODIMENTS O

In some embodiments, one of $q^3$, $q^4$ and $q^5$ is selected from $CH_2COOH$, $CH_2CONH_2$, $CH_2COO(CH_2)_{3-6}CH_3$, —$CH_2COO(CH_2)_{3-7}NH_2$, —$CH_2COO(CH_2)_{3-7}NHC(=NH)NH_2$, $CONH(CH_2)_{3-6}CH_3$, $CONH(CH_2)_{3-7}OH$, $CONH(CH_2)_{3-7}CH_2NH_2$, or $CONH(CH_2)_{3-7}CH_2NHC(=NH)NH_2$.

In some embodiments, at least one of $q_1$, $q_2$, $q_3$, $q_4$ and $q_5$ is F, and one of $q_3$, $q_4$ and $q_5$ is the group described by the general formula -$A^1$-$X_h$-$A^2$-$Y_n$.

In some embodiments, $q^3$ and $z^1$ is F, and one of $q^4$ and $q^5$ is the group described by the general formula -$A^1$-$X_h$-$A^2$-$Y_n$.

In some embodiments, $q^3$ is selected from the group described by the general formula -$A^1$-$X_h$-$A^2$-$Y_n$ and one of $z^1$, $z^2$, $q^2$, $q^2$, $q^4$ and $q^5$ is F.

In some embodiments, $q^3$ is the group described by the general formula -$A^1$-$X_h$-$A^2$-$Y_n$, $A^1$ is $CH_2$, h is 1, $X_h$ is —C(=O)OH, C(=O)$NH_2$—, —C(=O)O— or —C(=O)NR—, with each R being selected independently from H, methyl, ethyl, propyl, butyl, acetyl and 2-hydroxyethyl, in particular from H, methyl, ethyl, propyl, butyl, and one of $z^1$, $z^2$, $q^1$, $q^2$, $q^4$ and $q^5$ is F.

In some embodiments, two of $q^3$, $q^4$ and $q^5$ are a group described by the general formula -$A^1$-$X_h$-$A^2$-$Y_n$.

In some embodiments, $q^3$ is a group described by the general formula -$A^1$-$X_h$-$A^2$-$Y_n$, wherein $A^1$ is $CH_2$, h is 1, $X_h$ is —C(=O)OH, C(=O)NH—, —C(=O)O— or —C(=O)NR—, with each R being selected independently from H, methyl, ethyl, propyl, butyl, acetyl and 2-hydroxyethyl, in particular from H, methyl, ethyl, propyl and butyl, and one of $q^4$ or $q^5$ is a group described by the general formula -$A^1$-$X_h$-$A^2$-$Y_n$, as defined above, while the other one is H.

According to a second aspect of the invention, an oligomeric compound is provided comprising at least one tricyclic nucleoside having Formula II:

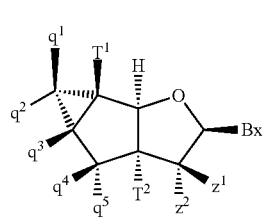

(II)

wherein independently for each tricyclic nucleoside of Formula II:
Bx is a heterocyclic base moiety;
one of $T^3$ and $T^4$ is an internucleoside linking group attaching the tricyclic nucleoside of Formula II to the oligomeric compound and the other of $T^3$ and $T^4$ is hydroxyl, a protected hydroxyl, a 5' or 3' terminal group or an internucleoside linking group attaching the tricyclic nucleoside to the oligomeric compound;
$q^1$ and $q^2$ are each, independently, H, F or Cl,
at least one of $q^3$, $q^4$ and $q^5$ is, independently, a group described by a general formula -$A^1$-$X_h$-$A^2$-$Y_n$, wherein
$A^1$ is a $C_k$-alkyl, $C_k$-alkenyl or $C_k$-alkynyl, with k being an integer selected from the range of 0 to 20,
$X_h$ is —C(=O)—, —C(=O)O—, —C(=O)NR—, —O—, —S—, —NR—, —C(=O)R, —C(=O)OR, —C(=O)$NR_2$—, —OR, —SR or —$NR_2$, with each R being selected independently from H, methyl, ethyl, propyl, butyl, acetyl and 2-hydroxyethyl, and h is 0 or 1,
$A^2$ is a $C_i$-alkyl, $C_i$-alkenyl or $C_i$-alkynyl, with i being an integer selected from the range of 0 to 20,
Y is a substituent group attached to any carbon atom on $A^1$ and/or $A^2$, selected from —F, —Cl, —Br, =O, —OR, —SR, —$NR_2$, —$NR_3$+, NHC(=NH)$NH_2$, —CN, —NC, —NCO, —NCS, —SCN, —COR, —$CO_2$R, $CONR_2$. —R, with each R being selected independently from H, methyl, ethyl, propyl, butyl, acetyl and 2-hydroxyethyl, and n is 0, 1, 2, 3, 4, 5 or 6,
wherein k+i equals at least 1,
the other ones of $q^3$, $q^4$ and $q^5$ are, independently, H, F or Cl,
one of $z^1$ and $z^2$ is H and the other of $z^1$ and $z^2$ is H, —OH, F, Cl, $OCH_3$, $OCF_3$, $OCH_2CH_3$, $OCH_2CF_3$, $OCH_2$—CH=$CH_2$, O($CH_2$)$_2$—$OCH_3$, O($CH_2$)$_2$—O($CH_2$)$_2$—N($CH_3$)$_2$, $OCH_2$C(=O)—N(H)$CH_3$, $OCH_2$C(=O)—N(H)—($CH_2$)$_2$—N($CH_3$)$_2$ or $OCH_2$—N(H)—C(=NH)$NH_2$.
and wherein said oligomeric compound comprises from 8 to 40 monomeric subunits.

In some embodiments of this aspect of the invention, Bx is a pyrimidine, substituted pyrimidine, purine or substituted purine. In some embodiments, Bx is selected from uracil, thymine, cytosine, 5-methylcytosine, adenine and guanine. In some embodiments, Bx is an aromatic heterocyclic moiety capable of forming base pairs when incorporated into DNA or RNA oligomers in lieu of the bases uracil, thymine, cytosine, 5-methylcytosine, adenine and guanine.

In some embodiments, one of $z^1$ and $z^2$ is F, $OCH_3$ or O($CH_2$)$_2$—$OCH_3$ for each tricyclic nucleoside of Formula II. In some embodiments, one of $z^1$ and $z^2$ is F for each tricyclic nucleoside of Formula II. In some embodiments, $z^1$ and $z^2$ are each F for each tricyclic nucleoside of Formula II. In some embodiments, one of $z^1$ and $z^2$ is F and the other one is H for each tricyclic nucleoside of Formula II. In some embodiments, $z^1$ and $z^2$ are each H for each tricyclic nucleoside of Formula II.

In some embodiments, $q^1$ and $q^2$ are each H for each tricyclic nucleoside of Formula II. In some embodiments, one of $q^1$ and $q^2$ is F and the other is H for each tricyclic nucleoside of Formula II. In some embodiments, $q^1$ and $q^2$ are each F for each tricyclic nucleoside of Formula II.

In some embodiments of this aspect of the invention, each internucleoside linking group is, independently, a phosphodiester internucleoside linking group or a phosphorothioate internucleoside linking group. In some embodiments, essentially each internucleoside linking group is a phosphorothioate internucleoside linking group.

In some embodiments, the oligomeric compound of the invention comprises a first region having at least two contiguous tricyclic nucleosides having Formula II. In some embodiments, the oligomeric compound of the invention comprises a first region having at least two contiguous tricyclic nucleosides having Formula II and a second region having at least two contiguous monomeric subunits wherein each monomeric subunit in the second region is a modified nucleoside different from the tricyclic nucleosides of Formula II of said first region. According to another alternative of this embodiment, the oligomeric compound comprises a third region located between said first and second regions wherein each monomer subunit in the third region is independently, a nucleoside or a modified nucleoside that is different from each tricyclic nucleoside of Formula II of the first region and each monomer subunit of the second region.

In some embodiments, the oligomeric compound of the invention comprises a gapped oligomeric compound having an internal region of from 6 to 14 contiguous monomer subunits flanked on each side by an external region of from 1 to 5 contiguous monomer subunits wherein each monomer subunit in each external region is a tricyclic nucleoside of Formula II and each monomer subunit in the internal region is, independently, a nucleoside or modified nucleoside. In some embodiments, said internal region comprises from about 8 to about 14 contiguous β-D-2'-deoxyribonucleosides. In some embodiments, said internal region comprises from about 9 to about 12 contiguous β-D-2'-deoxyribonucleosides.

In some embodiments, each tricyclic nucleoside of Formula II comprised in the oligomeric compound of the invention is selected from the embodiment group A above. In some embodiments, each tricyclic nucleoside of Formula II comprised in the oligomeric compound of the invention is selected from the embodiment group B above. In some embodiments, each tricyclic nucleoside of Formula II comprised in the oligomeric compound of the invention is selected from the embodiment group C above. In some embodiments, each tricyclic nucleoside of Formula II comprised in the oligomeric compound of the invention is selected from the embodiment group D above. In some embodiments, each tricyclic nucleoside of Formula II comprised in the oligomeric compound of the invention is selected from the embodiment group E above. In some embodiments, each tricyclic nucleoside of Formula II comprised in the oligomeric compound of the invention is selected from the embodiment group F above. In some embodiments, each tricyclic nucleoside of Formula II comprised in the oligomeric compound of the invention is selected from the embodiment group G above. In some embodiments, each tricyclic nucleoside of Formula II comprised in the oligomeric compound of the invention is selected from the embodiment group H above. In some embodiments, each tricyclic nucleoside of Formula II comprised in the oligomeric compound of the invention is selected from the embodiment group I above. In some embodiments, each tricyclic nucleoside of Formula II comprised in the oligomeric compound of the invention is selected from the embodiment group J above. In some embodiments, each tricyclic nucleoside of Formula II comprised in the oligomeric compound of the invention is selected from the embodiment group K above. In some embodiments, each tricyclic nucleoside of Formula II comprised in the oligomeric compound of the invention is selected from the embodiment group L above. In some embodiments, each tricyclic nucleoside of Formula II comprised in the oligomeric compound of the invention is selected from the embodiment group M above. In some embodiments, each tricyclic nucleoside of Formula II comprised in the oligomeric compound of the invention is selected from the embodiment group N above.

In some embodiments, $q^3$ is $C_1$-$C_{20}$ alkyl, substituted $C_1$-$C_{20}$ alkyl, $C_1$-$C_{20}$ alkenyl, substituted $C_1$-$C_{20}$ alkenyl, $C_1$-$C_{20}$ alkynyl, substituted $C_1$-$C_{20}$ alkynyl, $C_1$-$C_{20}$ alkoxy, substituted $C_1$-$C_{20}$ alkoxy, amino, substituted amino, thiol or substituted thiol for each tricyclic nucleoside of Formula II. In some embodiments, one of $q^4$ and $q^5$ is H and the other of $q^4$ and $q^5$ is $C_1$-$C_{20}$ alkyl, substituted $C_1$-$C_{20}$ alkyl, $C_1$-$C_{20}$ alkenyl, substituted $C_1$-$C_{20}$ alkenyl, $C_1$-$C_{20}$ alkynyl, substituted $C_1$-$C_{20}$ alkynyl, $C_1$-$C_{20}$ alkoxy, substituted $C_1$-$C_{20}$ alkoxy, amino, substituted amino, thiol or substituted thiol for each tricyclic nucleoside of Formula II.

In some embodiments, $q^3$ is $C_1$-$C_6$ alkyl, substituted $C_1$-$C_6$ alkyl, $C_1$-$C_6$ alkenyl, substituted $C_1$-$C_6$ alkenyl, $C_1$-$C_6$ alkynyl, substituted $C_1$-$C_6$ alkynyl, $C_1$-$C_6$ alkoxy, substituted $C_1$-$C_6$ alkoxy, amino, substituted amino, thiol or substituted thiol for each tricyclic nucleoside of Formula II. In some embodiments, one of $q^4$ and $q^5$ is H and the other of $q^4$ and $q^5$ is $C_1$-$C_6$ alkyl, substituted $C_1$-$C_6$ alkyl, $C_1$-$C_6$ alkenyl, substituted $C_1$-$C_6$ alkenyl, $C_1$-$C_6$ alkynyl, substituted $C_1$-$C_6$ alkynyl, $C_1$-$C_6$ alkoxy, substituted $C_1$-$C_6$ alkoxy, amino, substituted amino, thiol or substituted thiol for each tricyclic nucleoside of Formula II.

In some embodiments, the oligomeric compound of the invention comprises one or several nucleotide blocks selected from the group consisting of a.

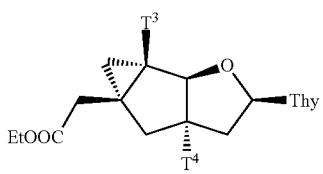

b.

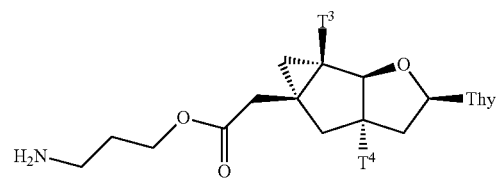

c.

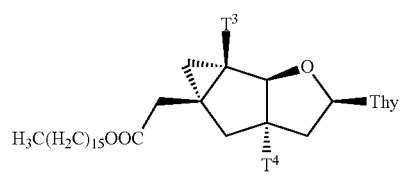

wherein $T^3$ and $T^4$ have the meanings outlined above.

In some embodiments, at least two of $q^3$, $q^4$ and $q^5$ are a group described by the general formula formula -$A^1$-$X_h$-$A^2$-$Y_n$ for each tricyclic nucleoside of Formula II.

According to yet another aspect of the invention, a method for solid-phase synthesis of an oligonucleotide is provided, comprising the use of a trycyclic nucleoside according to the first aspect of the invention. According to this aspect of the invention, a nucleoside according to the first aspect of the invention, any reactive OH, NH$_2$ or other reactive group being protected by a protective group as laid out elsewhere herein, is used e.g. as a phosphoamidite activated building block and incorporated into the nascent oligomeric chain. The methods and reagents useful for such purpose are known to the skilled person and are exemplified by the examples provided herein.

In certain embodiments, gapped oligomeric compounds are provided comprising an internal region of from 6 to 14 contiguous monomer subunits flanked on each side by an external region of from 1 to 5 contiguous monomer subunits wherein each monomer subunit in each external region is a tricyclic nucleoside of Formula II and each monomer subunit in the internal region is, independently, a nucleoside or modified nucleoside. In certain embodiments, the internal region comprises from about 8 to about 14 contiguous β-D-2'-deoxyribonucleosides. In certain embodiments, the internal region comprises from about 9 to about 12 contiguous β-D-2'-deoxyribonucleosides.

In certain embodiments, methods of inhibiting gene expression are provided comprising contacting a cell with an oligomeric compound comprising a 5' modified nucleoside as provided herein or a double stranded composition comprising at least one oligomeric compound comprising a 5' modified nucleoside as provided herein wherein said oligomeric compound comprises from about 8 to about 40 monomeric subunits and is complementary to a target RNA. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function. In certain embodiments, the methods further comprise detecting the levels of target RNA.

In certain embodiments, in vitro methods of inhibiting gene expression are provided comprising contacting one or more cells or a tissue with an oligomeric compound or double stranded composition as provided herein.

In certain embodiments, oligomeric compounds or a double stranded composition as provided herein are used for use in an in vivo method of inhibiting gene expression said method comprising contacting one or more cells, a tissue or an animal with one of the oligomeric compounds or a double stranded composition as provided herein.

In certain embodiments, oligomeric compounds and double stranded compositions as provided herein are used in medical therapy.

In certain embodiments, for each tricyclic nucleoside of Formula II, the placement of the substituent group generally defined as -$A^1$-$X_n$-$A^2$-$Y_n$ at one of the substituent positions $q^3$, $q^4$, $q^5$ enhances biodistribution, cellular uptake or delivery of oligomers. In certain embodiments, for each tricyclic nucleoside of Formula II, the placement of the substituent group F at one of the substituent positions $q^1$, $q^2$, $q^3$, $q^4$, $q^5$, $z^1$ or $z^2$ enhances one or more properties of the oligomeric compound such as for example, and without limitation, stability, nuclease resistance, binding affinity, specificity, absorption, cellular distribution, cellular uptake, charge, pharmacodynamics and pharmacokinetics. In certain embodiments, for each tricyclic nucleoside of Formula II, it is expected that the placement of F at one of the substituent positions $q^1$, $q^2$, $q^3$, $q^4$, $q^5$, $z^1$ or $z^2$ will enhance the binding affinity.

DETAILED DESCRIPTION OF THE INVENTION

Provided herein are novel tricyclic nucleosides having Formula I and oligomeric compounds prepared therefrom. The tricyclic nucleosides having Formula I are useful for enhancing one or more properties of the oligomeric compounds they are incorporated into such as but not limited to nuclease resistance, cell entry, intracellular delivery, transport in the body, particularly in the blood, ease of pharmaceutical formulation and drug metabolism. In certain embodiments, the oligomeric compounds provided herein hybridize to a portion of a target RNA resulting in loss of normal function of the target RNA. In certain embodiments, tricyclic nucleosides having Formula I are provided that can be incorporated into antisense oligomeric compounds to reduce target RNA, such as messenger RNA, in vitro and in vivo. In one aspect the reduction or loss of function of target RNA is useful for inhibition of gene expression via numerous pathways. Such pathways include for example the steric blocking of transcription and/or translation of mRNA and cleavage of mRNA via single or double stranded oligomeric compounds. The oligomeric compounds provided herein are also expected to be useful as primers and probes in diagnostic applications.

In certain embodiments, double stranded compositions are provided wherein each double stranded composition comprises:
 a first oligomeric compound and a second oligomeric compound wherein the first oligomeric compound is complementary to the second oligomeric compound and the second oligomeric compound is complementary to a nucleic acid target;
 at least one of the first and second oligomeric compounds comprises at least one tricyclic nucleoside of Formula II; and
 wherein said compositions optionally comprise one or more terminal groups.

As used herein the term "alkyl," refers to a saturated straight or branched hydrocarbon radical containing up to 24, particularly up to 20, carbon atoms. Examples of alkyl groups include without limitation, methyl, ethyl, propyl, butyl, isopropyl, n-hexyl, octyl, decyl, dodecyl and the like. Alkyl groups typically include from 1 to about 20 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms.

As used herein the term "alkenyl," refers to a straight or branched hydrocarbon chain radical containing up to 24, particularly up to 20, carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 20 carbon atoms, more typically from 2 to about 12 carbon atoms with from 2 to about 6 carbon atoms being more preferred.

As used herein the term "alkynyl," refers to a straight or branched hydrocarbon radical containing up to 24, particularly up to 20, carbon atoms and having at least one carbon-carbon triple bond. Examples of alkynyl groups include, without limitation, ethynyl, 1-propynyl, 1-butynyl, and the like. Alkynyl groups typically include from 2 to about 20 carbon atoms, more typically from 2 to about 12 carbon atoms with from 2 to about 6 carbon atoms being more preferred.

As used herein the term "alkoxy," refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein the term "aminoalkyl" refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein the term "protecting group," refers to a labile chemical moiety, which is known in the art to protect reactive groups including without limitation, hydroxyl, amino and thiol groups, against undesired reactions during synthetic procedures. Protecting groups are typically used selectively to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1 (2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyl-diphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The compounds described herein contain one or more asymmetric centers and thus give rise to enantiomers, diastereomers, and other stereoisomeric forms that may be defined, in terms of absolute stereochemistry, as (R) or (S). Included herein are all such possible isomers, as well as their racemic and optically pure forms. The configuration of any carbon-carbon double bond appearing herein is selected for convenience only and is not intended to limit a particular configuration unless the text so states.

In some embodiments, an alkyl, alkenyl or alkynyl group as used herein may optionally include one or more further substituent groups. The terms "substituent" and "substituent group" are meant to include groups that are typically added to other groups or parent compounds to enhance desired properties or provide other desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Substituent groups amenable herein include without limitation, halogen, oxygen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), isocyano (—NC), cyanato (—OCN), isocyanato (—NCO), thiocyanato (—SCN); isothiocyanato (—NCS); carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)($R_{cc}$)), guanidinyl (—N($R_{bb}$)C(=$NR_{bb}$)—N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

In some embodiments, an alkyl, alkenyl or alkynyl group as used herein contains one, two or three further substituent groups selected independently from the group of —F, —Cl, —Br, =O, $NH_2$, SH, OH, OR, SR, NHR, —$NR_2$, —CN, —NC, —NCO, —NCS, —SCN, —COR, —$CO_2R$, $CONR_2$, —R with R being selected from methyl, ethyl, propyl, butyl, acetyl and 2-hydroxyethyl.

In some embodiments, an alkyl, alkenyl or alkynyl group as used herein contains no further substituent groups but consists only of carbon and hydrogen atoms.

As used herein, the term "nucleobase" refers to unmodified or naturally occurring nucleobases which include, but are not limited to, the purine bases adenine (A) and guanine (G), and the pyrimidine bases thymine (T), cytosine (C) and uracil (U). As used herein, the term "heterocyclic base moiety" refers to unmodified or naturally occurring nucleobases as well as modified or non-naturally occurring nucleobases and synthetic mimetics thereof (such as for example phenoxazines). In certain embodiments, a heterocyclic base moiety is any heterocyclic system that contains one or more atoms or groups of atoms capable of hydrogen bonding to a heterocyclic base of a nucleic acid.

In certain embodiments, heterocyclic base moieties include without limitation modified nucleobases such as 5-methylcytosine (5-me-C), 5-hydroxymethyl cytosine, xanthine, hypoxanthine, 2-amino-adenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

In certain embodiments, heterocyclic base moieties include without limitation tricyclic pyrimidines such as 1,3-diazaphenoxazine-2-one, 1,3-diazaphenothiazine-2-one and 9-(2-aminoethoxy)-1,3-diazaphenoxazine-2-one (G-clamp). Heterocyclic base moieties also include those in which the purine or pyrimidine base is replaced with other heterocycles, for example 7-deaza-adenine, 7-deazaguanosine, 2-aminopyridine and 2-pyridone. Further heterocyclic base moieties include without limitation those known to the art skilled (see for example: U.S. Pat. No. 3,687,808; Swayze et al., *The Medicinal Chemistry of Oligonucleotides* in Antisense a Drug Technology, Chapter 6, pages 143-182, Crooke, S. T., ed., 2008); *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-302.

As used herein the term "sugar moiety" refers to naturally occurring sugars having a furanose ring, synthetic or non-naturally occurring sugars having a modified furanose ring and sugar surrogates wherein the furanose ring has been replaced with a cyclic ring system such as for example a morpholino or hexitol ring system or a non-cyclic sugar surrogate such as that used in peptide nucleic acids. Illustrative examples of sugar moieties useful in the preparation of oligomeric compounds include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose), tricyclic modified sugars (such as the 2'-O—CH$_2$-4' or 2'-O—(CH$_2$)$_2$-4' bridged ribose derived tricyclic sugars) and sugar surrogates (such as for example when the ribose ring has been replaced with a morpholino, a hexitol ring system or an open non-cyclic system).

As used herein, the term "nucleoside" refers to a nucleobase-sugar combination. The two most common classes of such nucleobases are purines and pyrimidines.

As used herein, the term nucleotide refers to a nucleoside further comprising a modified or unmodified phosphate internucleoside linking group or a non-phosphate internucleoside linking group. For nucleotides that include a pentofuranosyl sugar, the internucleoside linking group can be linked to either the 2', 3' or 5' hydroxyl moiety of the sugar. The phosphate and or a non-phosphate internucleoside linking groups are routinely used to covalently link adjacent nucleosides to one another to form a linear polymeric compound.

The term "nucleotide mimetic" as used herein is meant to include monomers that incorporate into oligomeric compounds with sugar and linkage surrogate groups, such as for example peptide nucleic acids (PNA) or morpholinos (linked by —N(H)—C(=O)—O—). In general, the heterocyclic base at each position is maintained for hybridization to a nucleic acid target but the sugar and linkage is replaced with surrogate groups that are expected to function similar to native groups but have one or more enhanced properties.

As used herein the term "nucleoside mimetic" is intended to include those structures used to replace the sugar and the base at one or more positions of an oligomeric compound. Examples of nucleoside mimetics include without limitation nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a group such as for example a morpholino, a cyclohexenyl or a bicyclo[3.1.0]hexyl.

As used herein the term "modified nucleoside" is meant to include all manner of modified nucleosides that can be incorporated into an oligomeric compound using oligomer synthesis. The term is intended to include modifications made to a nucleoside such as modified stereochemical configurations, one or more substitutions, and deletion of groups as opposed to the use of surrogate groups which are described elsewhere herein. The term includes nucleosides having a furanose sugar (or 4'-S analog) portion and can include a heterocyclic base or can be an abasic nucleoside. One group of representative modified nucleosides includes without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as for example, bicyclic nucleosides wherein the sugar moiety has a 2'-O—CHR$_a$-4' bridging group, wherein R$_a$ is H, alkyl or substituted alkyl) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein. As used herein the term "monomer subunit" is meant to include all manner of monomer units that are amenable to oligomer synthesis with one preferred list including monomer subunits such as β-D-ribonucleosides, β-D-2'-deoxyribnucleosides, modified nucleosides, including substituted nucleosides (such as 2', 5' and bis substituted nucleosides), 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides, nucleoside mimetics, nucleosides having sugar surrogates and the tricyclic nucleosides as provided herein. Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

As used herein the term "reactive phosphorus" is meant to include groups that are covalently linked to a monomer subunit that can be further attached to an oligomeric compound that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[(CH(CH$_3$)$_2$]$_2$]O(CH$_2$)$_2$CN) and H-phosphonate (—O*—P(=O)(H)OH), wherein the O* is provided from the Markush group for the monomer. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield, phosphodiester or phosphorothioate internucleoside linkages. Additional reactive phosphates and phosphites are disclosed in Tetrahedron Report Number 309 (Beaucage and Iyer, *Tetrahedron*, 1992, 48, 2223-2311).

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and $CH_2$ component parts.

As used herein, the term "oligomeric compound" refers to a contiguous sequence of linked monomer subunits. Each linked monomer subunit normally includes a heterocyclic base moiety but monomer subunits also includes those without a heterocyclic base moiety such as abasic monomer subunits. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleoside mimetics and or nucleosides having sugar surrogate groups.

In certain embodiments, oligomeric compounds comprise a plurality of monomer subunits independently selected from naturally occurring nucleosides, non-naturally occurring nucleosides, modified nucleosides, nucleoside mimetics, and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-$CH_2$—C(=O)—N(H)-5'), amide-4 (3'-$CH_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

As used herein the term "phosphate moiety" refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

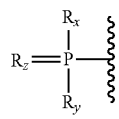

wherein:

$R_x$ and $R_y$ are each, independently, hydroxyl, protected hydroxyl group, thiol, protected thiol group, $C_1$-$C_6$ alkyl, substituted $C_1$-$C_6$ alkyl, $C_1$-$C_6$ alkoxy, substituted $C_1$-$C_6$ alkoxy, a protected amino or substituted amino; and $R_z$ is O or S.

As a monomer such as a phosphoramidite or H-phosphonate the protected phosphorus moiety is preferred to maintain stability during oligomer synthesis. After incorporation into an oligomeric compound the phosphorus moiety can include deprotected groups.

Phosphorus moieties included herein can be attached to a monomer, which can be used in the preparation of oligomeric compounds, wherein the monomer may be attached using O, S, $NR_d$ or $CR_eR_f$, wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

The relative ability of a chemically-modified oligomeric compound to bind to complementary nucleic acid strands, as compared to natural oligonucleotides, is measured by obtaining the melting temperature of a hybridization complex of said chemically-modified oligomeric compound with its complementary unmodified target nucleic acid. The melting temperature ($T_m$), a characteristic physical property of double helixes, denotes the temperature in degrees centigrade at which 50% helical versus coiled (unhybridized) forms are present. $T_m$ (also commonly referred to as binding affinity) is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$.

It is known in the art that the relative duplex stability of an antisense compound:RNA target duplex can be modulated through incorporation of chemically-modified nucleosides into the antisense compound. Sugar-modified nucleosides have provided the most efficient means of modulating the $T_m$ of an antisense compound with its target RNA. Sugar-modified nucleosides that increase the population of or lock the sugar in the C3'-endo (Northern, RNA-like sugar pucker) configuration have predominantly provided a per modification $T_m$ increase for antisense compounds toward a complementary RNA target. Sugar-modified nucleosides that increase the population of or lock the sugar in the C2'-endo (Southern, DNA-like sugar pucker) configuration predominantly provide a per modification Tm decrease for antisense compounds toward a complementary RNA target. The sugar pucker of a given sugar-modified nucleoside is not the only factor that dictates the ability of the nucleoside to increase or decrease an antisense compound's $T_m$ toward complementary RNA. For example, the sugar-modified nucleoside tricycloDNA is predominantly in the C2'-endo conformation, however it imparts a 1.9 to 3° C. per modification increase in $T_m$ toward a complementary RNA. Another example of a sugar-modified high-affinity nucleoside that does not adopt the C3'-endo conformation is α-L-LNA (described in more detail herein).

As used herein, "$T_m$" (melting temperature) is the temperature at which the two strands of a duplex nucleic acid separate. The $T_m$ is often used as a measure of duplex stability of an antisense compound toward a complementary RNA molecule.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases or more broadly, heterocyclic base moieties, comprising certain modifications may maintain the ability to pair with a counterpart nucleobase and thus, are still capable of complementarity.

As used herein, "non-complementary" in reference to nucleobases refers to a pair of nucleobases that do not form hydrogen bonds with one another or otherwise support hybridization.

As used herein, "complementary" in reference to linked nucleosides, oligonucleotides, oligomeric compounds, or nucleic acids, refers to the capacity of an oligomeric compound to hybridize to another oligomeric compound or nucleic acid through nucleobase or more broadly, heterocyclic base, complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid. Alternatively, the oligomeric compound may inhibit the activity the target nucleic acid through an occupancy-based method, thus interfering with the activity of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

As used herein, the term "pharmaceutically acceptable salts" refers to salts that retain the desired activity of the compound and do not impart undesired toxicological effects thereto. The term "pharmaceutically acceptable salt" includes a salt prepared from pharmaceutically acceptable non-toxic acids or bases, including inorganic or organic acids and bases.

Pharmaceutically acceptable salts of the oligomeric compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in certain embodiments the oligomeric compounds described herein are in the form of a sodium salt.

In certain embodiments, oligomeric compounds provided herein comprise from about 8 to about 80 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—$CH_2$—O—$Si(iPr)_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent. In the case of oligomeric compounds targeted to microRNA, candidate modulators may be evaluated by the extent to which they increase the expression of a microRNA target RNA or protein (as interference with the activity of a microRNA will result in the increased expression of one or more targets of the microRNA).

As used herein, "expression" refers to the process by which a gene ultimately results in a protein. Expression includes, but is not limited to, transcription, splicing, post-transcriptional modification, and translation.

Suitable target segments may also be combined with their respective complementary oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature*, 1998, 391, 806-811; Timmons and Fire, *Nature*, 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.*, 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The oligomeric compounds provided herein can also be applied in the areas of drug discovery and target validation. In certain embodiments, provided herein is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound as provided herein. These methods can also be performed in parallel or in combination with other experiments to determine the function of unknown genes for the process of target validation or to determine the validity of a particular gene product as a target for treatment or prevention of a particular disease, condition, or phenotype. In certain embodiments, oligomeric compounds are provided for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds are provided herein that may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., *Nature*, 2001, 411, 494-498; Nishikura et al., *Cell*, 2001, 107, 415-416; and Bass et al., *Cell*, 2000, 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or other therapeutics as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of oligomeric compounds as provided herein, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. USA*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the tricyclic nucleosides provided herein and may also include other monomer subunits including but not limited to nucleosides, modified nucleosides, nucleosides comprising sugar surrogate groups and nucleoside mimetics.

While in certain embodiments, oligomeric compounds provided herein can be utilized as described, the following examples serve only to illustrate and are not intended to be limiting. Wherever alternatives for single separable features such as, for example, any of the alternatives given for $q^1$, $q^4$, $T^1$, or $T^2$, or Bx, or $A^1$, $A^2$, X, h, Y or n, are laid out herein as "embodiments", it is to be understood that such alternatives may be combined freely to form discrete embodiments of the invention disclosed herein.

EXAMPLES

General Methods $^1$H and $^{13}$C NMR spectra were recorded on a 300 MHz and 75 MHz Bruker spectrometer, respectively.
Synthesis of Nucleoside Phosphoramidites The preparation of nucleoside phosphoramidites is performed following procedures that are illustrated herein and in the art such as but not limited to U.S. Pat. No. 6,426,220 and WO02/36743.
Synthesis of Oligomeric Compounds The oligomeric compounds used in accordance with this invention may be conveniently and routinely made through solid phase synthesis.

Oligomeric compounds: Unsubstituted and substituted phosphodiester (P=O) oligomeric compounds can be synthesized on an automated DNA synthesizer (for example Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M $NH_4OAc$ solution. Phosphinate internucleoside linkages can be prepared as described in U.S. Pat. No. 5,508,270. Alkyl phosphonate internucleoside linkages can be prepared as described in U.S. Pat. No. 4,469,863. 3'-Deoxy-3'-methylene phosphonate internucleoside linkages can be prepared as described in U.S. Pat. No. 5,610,289 or 5,625,050. Phosphoramidite internucleoside linkages can be prepared as described in U.S. Pat. No. 5,256,775 or U.S. Pat. No. 5,366,878. Alkylphosphonothioate internucleoside linkages can be prepared as described in published PCT applications PCT/US94/00902 and PCT/US93/06976 (published as WO 94/17093 and WO 94/02499, respectively). 3'-Deoxy-3'-amino phosphoramidate internucleoside linkages can be prepared as described in U.S. Pat. No. 5,476,925. Phosphotriester internucleoside linkages can be prepared as described in U.S. Pat. No. 5,023,243. Borano phosphate internucleoside linkages can be prepared as described in U.S. Pat. Nos. 5,130,302 and 5,177,198. Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564. Ethylene oxide internucleoside linkages can be prepared as described in U.S. Pat. No. 5,223,618.

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectrometry (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 1

Preparation of Compound 10

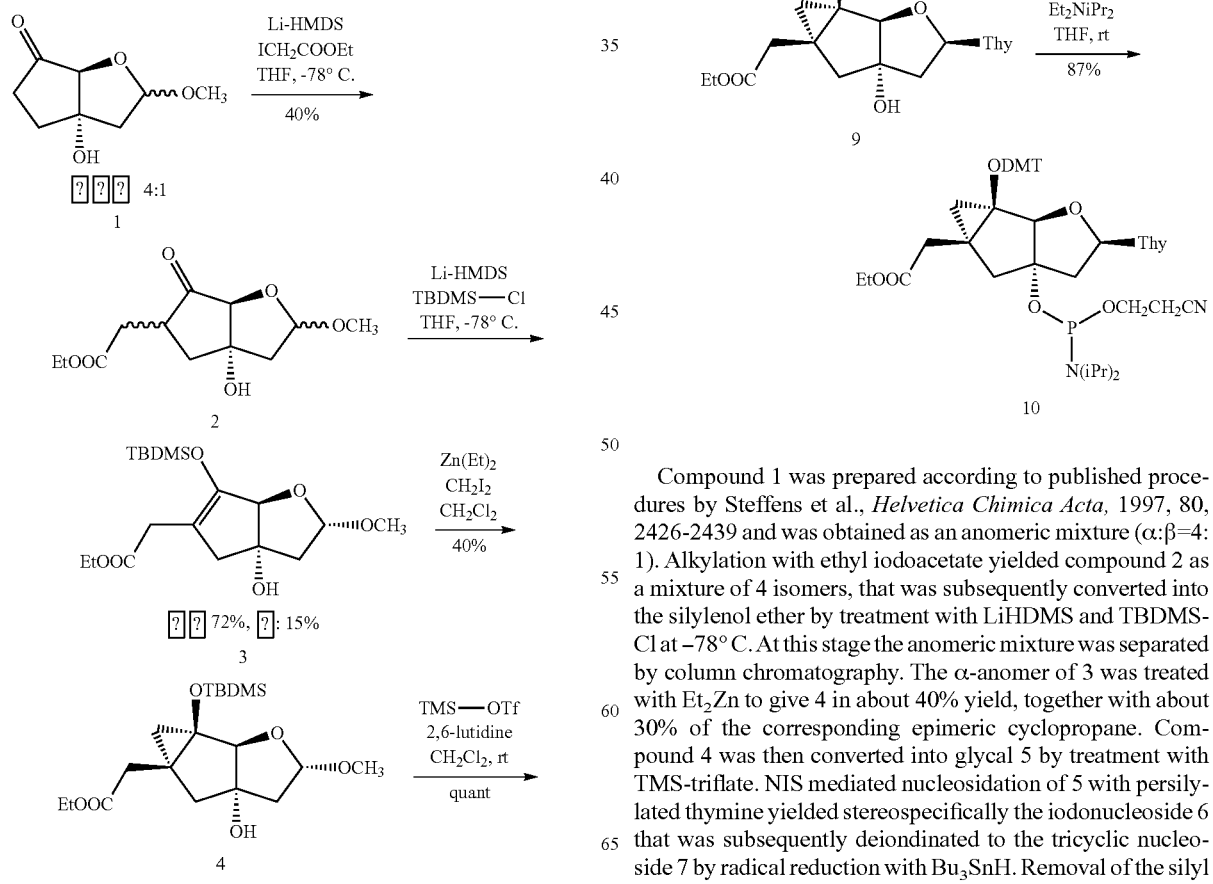

Compound 1 was prepared according to published procedures by Steffens et al., *Helvetica Chimica Acta*, 1997, 80, 2426-2439 and was obtained as an anomeric mixture (α:β=4:1). Alkylation with ethyl iodoacetate yielded compound 2 as a mixture of 4 isomers, that was subsequently converted into the silylenol ether by treatment with LiHDMS and TBDMS-Cl at −78° C. At this stage the anomeric mixture was separated by column chromatography. The α-anomer of 3 was treated with Et$_2$Zn to give 4 in about 40% yield, together with about 30% of the corresponding epimeric cyclopropane. Compound 4 was then converted into glycal 5 by treatment with TMS-triflate. NIS mediated nucleosidation of 5 with persilylated thymine yielded stereospecifically the iodonucleoside 6 that was subsequently deiodinated to the tricyclic nucleoside 7 by radical reduction with Bu$_3$SnH. Removal of the silyl protecting groups with HF in pyridine afforded compound 8 that was subsequently tritylated and phosphitylated to give the desired phosphoramidite 10. All the structures were confirmed by spectral analysis.

Example 2

Preparation of Compound 15

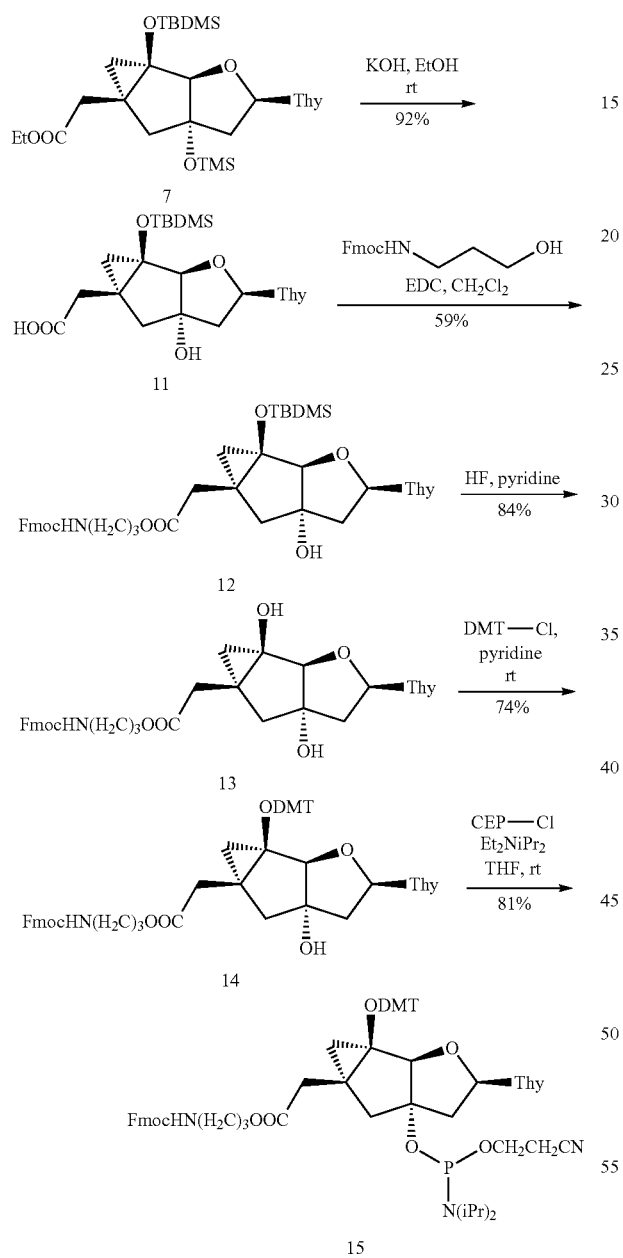

Compound 7 was prepared as illustrated in Example 1. Basic hydrolysis of 7 with KOH afforded acid 11 that was converted into compound 12 by treatment with Fmoc protected aminopropanol and the condensing agent EDC. Removal of the silyl protecting groups followed by tritylation and phosphitylation yielded the desired phosphoramidite 15. All the structures were confirmed by spectral analysis.

Example 3

Preparation of Compound 19

Compound 11 was prepared as illustrated in Example 2 and was esterified to compound 16 with hexadecanol and EDC as condensing agent. Desilylation with HF followed by tritylation with DMT-Cl and phosphitylation lead to the desired phosphoramidite 19. All the structures were confirmed by spectral analysis.

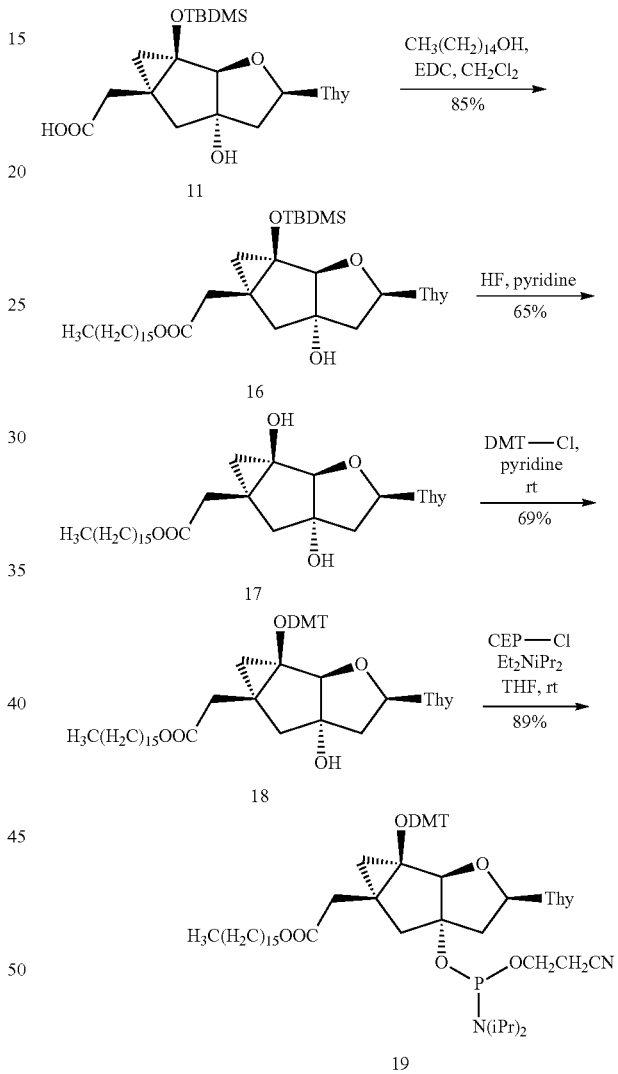

Example 4

Preparation of compound 21

Compound 11 was prepared as illustrated in Example 2 and was converted to compound 20 with the singly protected 1,3-diaminopropane and EDC as condensing agent. Desilylation with HF afforded compound 21. All the structures were confirmed by spectral analysis.

33

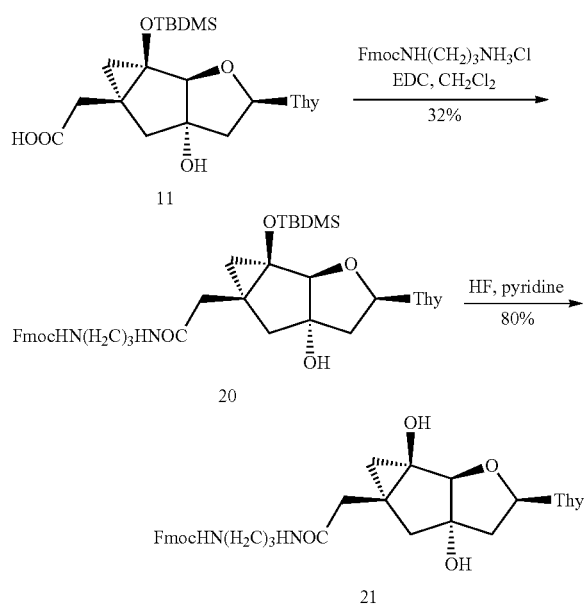

Example 5

Preparation of Oligomeric Compounds

Following synthetic procedures well known in the art, some of which are illustrated herein, oligomeric compounds are prepared having at least one tricyclic nucleosides, using one or more of the phosphoramidite compounds illustrated in the Examples such as DMT phosphoramidites (see Compound 10, Compound 15 or Compound 19).

Example 6

Preparation of Oligomeric Compounds for Tm Study

Following standard automated DNA synthesis protocols oligomeric compounds were prepared comprising one or more tricyclic nucleosides for Tm studies. After cleavage from the solid support, the oligomeric compounds were purified by ion exchange HPLC and analyzed by LCMS using standard procedures. The Tm of the modified 10mer oligomeric compounds were compared to an unmodified 10mer DNA oligonucleotide when duplexed to either DNA or RNA. Tm's were determined using a Cary 100 Bio spectrophotometer with the Cary Win UV thermal program was used to measure absorbance vs. temperature. For the $T_m$ experiments, the oligomeric compounds were prepared at a concentration of 1.2 M in a buffer of 150 mM NaCl, 10 mM phosphate, 0.1 mM EDTA at pH 7. The concentration determined at 85° C. was 1.2 M after mixing of equal volumes of selected oligomeric compound and complementary RNA or DNA. The oligomeric compounds were hybridized with a complementary RNA or DNA by heating the duplex to 90° C. for 5 minutes and then cooling to room temperature. $T_m$ measurements were taken using a spectrophotometer while the duplex solution was heated in a cuvette at a rate of 0.5° C./min starting at 15° C. until the temperature was 85° C. $T_m$ values were determined using Vant Hoff calculations ($A_{260}$ vs temperature curve) using non self-complementary sequences where the minimum absorbance related to the duplex and the

34 maximum absorbance related to the non-duplex single strand are manually integrated into the program.

| SEQ ID NO. | Sequence (5' to 3') | ΔTm/mod (° C.) vs DNA | ΔTm/mod (° C.) vs RNA |
|---|---|---|---|
| A01 | AACTGTCACG | 0 | 0 |
| A02 | AACTGT$_b$CACG | -0.9 | +0.4 |
| A03 | AACTGT$_d$CACG | +0.5 | +2.1 |
| A04 | AACT$_b$GTCACG | +0.1 | +2.4 |
| A05 | AACT$_d$GTCACG | +0.4 | +2.4 |
| A06 | AACT$_b$GT$_b$CACG | -0.7 | +0.5 |
| A07 | AACT$_c$GT$_c$CACG | -1.0 | +1.3 |
| A08 | AACT$_d$GT$_d$CACG | -0.6 | +1.2 |
| A09 | AACT$_e$GT$_e$CACG | -13.0 | -10.2 |
| A10 | AACT$_f$GT$_f$CACG | -2.0 | +1.3 |
| A11 | A$_d$A$_d$C$_a$T$_a$G$_a$T$_a$C$_a$A$_a$C$_a$G$_a$ | +1.3 | +2.1 |
| A12 | A$_d$A$_d$C$_a$T$_a$G$_a$T$_d$C$_a$A$_a$C$_a$G$_a$ | -2.8 | -0.6 |
| A13 | A$_d$A$_d$C$_a$T$_d$G$_a$T$_a$C$_a$A$_a$C$_a$G$_a$ | -3.8 | -2.6 |
| A14 | A$_d$A$_d$C$_a$T$_b$G$_a$T$_b$C$_a$A$_a$C$_a$G$_a$ | +1.1 | +2.0 |
| A15 | A$_d$A$_d$C$_a$T$_c$G$_a$T$_c$C$_a$A$_a$C$_a$G$_a$ | +1.1 | +2.0 |
| A16 | A$_d$A$_d$C$_a$T$_d$G$_a$T$_d$C$_a$A$_a$C$_a$G$_a$ | +1.1 | +2.3 |

The Tms of the unmodified oligomeric compound A01 are 47.9° C. and 48.3° C. duplexed with DNA or RNA respectively. Each internucleoside linking group is a phosphodiester. Each nucleoside not followed by a subscript is a β-D-2'-deoxyribonucleoside and each nucleoside followed by a subscript "a" to subscript "f" are as defined below.

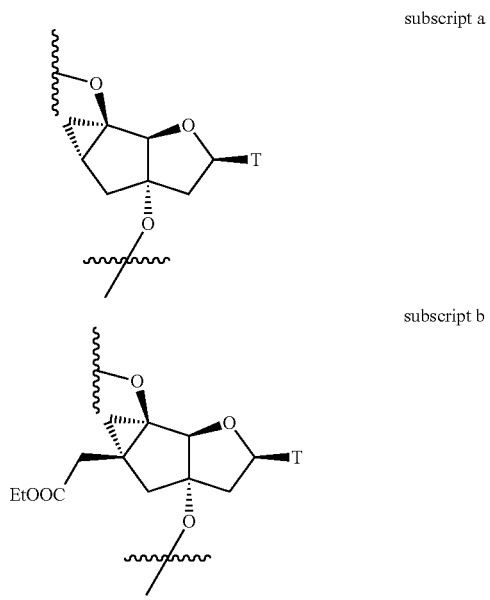

-continued subscript c

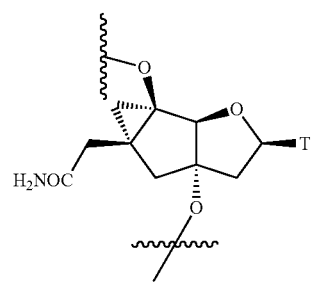

subscript d

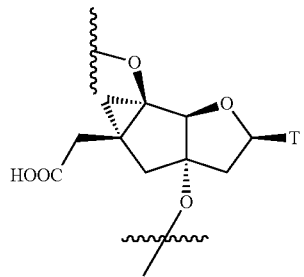

subscript e

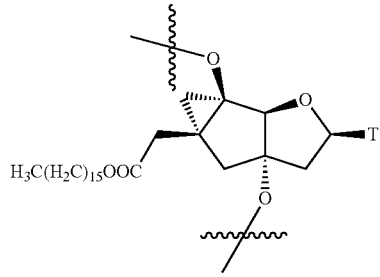

subscript f

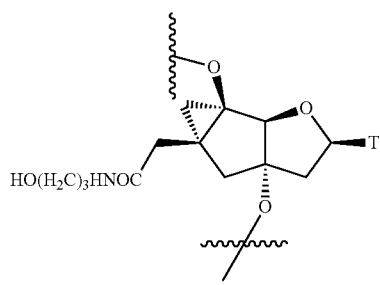

Example 7

Preparation of Oligomeric Compounds for Uptake Studies into HeLa Cells

Hela cells were grown at 37° C. in Dulbecco's Modified Eagle's Medium (DMEM, Invitrogen) supplemented with 10% (v/v) Fetal Calf Serum (Amimed), 100 units/ml penicillin (Invitrogen) and 100 μg/ml streptomycin (Invitrogen). For transfection experiments, 1×10$^5$ cells were seeded in duplicate in six well plates, half of them containing cover slips, 24 h before transfection. Then, the medium was replaced by a solution of oligonucleotide (10 μM final concentration) having the sequence 5'-T-t-T-t-T-t-T-t-T-t-FAM-3' where T is deoxythymidine and t is either tc$^{ee}$T (subscript b of example 6) (SEQ ID NO:17), tc$^{hd}$T (subscript e of example 6) (SEQ ID NO:18) or tcT (subscript a of example 6) (SEQ ID NO:19) and FAM is 6-10 carboxyfluorescein, ire DMEM +/+(FCS, P/S).

The transfection medium was removed after 48 h at 37° C. and cells were washed with 2×1 ml PBS and resuspended in 1 ml fresh DMEM +/+. Fixation of the cells on the cover slips was carried out using a solution of paraformaldehyde (1 ml, 3.7% in PBS) for 10 min followed by washing with PBS (2×1 ml), permeabilization of the cell membrane with Triton x-100 (0.2%, Promega) for 10 min and washing with PBS (2×1 ml). The cover slips were treated with a few drops of polyvinylalcohol (Mowiol) and nuclear stain 40,60-diamidino-2-phenylindole (DAPI). Cells were analyzed by fluorescence microscopy (Leica DMI6000 B, Leica Microsystems; software: Leica Application Suite) 48 h post transfection.

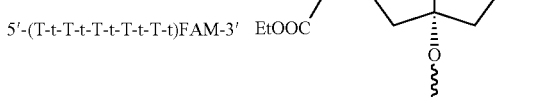

5'-(T-t-T-t-T-t-T-t-T-t)FAM-3'    EtOOC

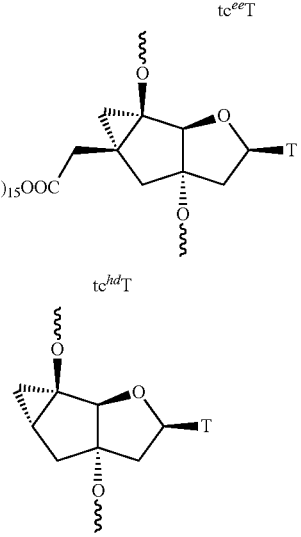

t = tc
T = natural dT

The microscopy pictures show strong fluorescein fluorescence in the cytosol of cells treated with oligonucleotides containing tc$^{hd}$T (subscript e of example 6) (SEQ ID NO: 18), while no fluorescence is observed when oligonucleotides containing tc$^{ee}$T (subscript b of example 6) or tcT (subscript a of example 6) (SEQ ID NO:19) were used.

Example 8

Preparation of Oligomeric Compounds for Uptake Studies into HEK293T Cells

HEK293T cells were grown at 37° C. in Dulbecco's Modified Eagle's Medium (DMEM, Invitrogen) supplemented with 10% (v/v) Fetal Calf Serum (Amimed), 100 units/ml penicillin (Invitrogen) and 100 μg/ml streptomycin (Invitrogen). For transfection experiments, 2×10$^5$ cells were seeded in duplicate in six-well plates, half of them containing cover slips, 24 h before transfection. Then, the medium was replaced by a solution of oligonucleotide (10 μM final concentration) having the sequence 5'-T-t-T-t-T-t-T-t-T-t-FAM-3' where T is deoxythymidine and t is either unmodified deoxythymidine (SEQ ID NO:20), tc$^{ee}$T (subscript b of example 6) (SEQ ID NO:17), tc$^{hd}$T (subscript e of example 6) (SEQ ID NO:18) or tcT (subscript a of example 6) (SEQ ID NO:19) and FAM is 6-carboxyfluorescein, in DMEM +/+(FCS, P/S). The transfection medium was removed after 48 h at 37° C. and cells were washed with 2×1 ml PBS and resuspended in 1 ml fresh DMEM +/+. Fixation of the cells on the cover slips was carried out using a solution of paraformaldehyde (1 ml, 3.7% in PBS) for 10 min followed by washing with PBS (2×1 ml), permeabilization of the cell membrane with Triton x-100 (0.2%, Promega) for 10 min and washing with PBS (2×1 ml). The cover slips were treated with a few drops of polyvinylalcohol (Mowiol) and nuclear stain 40,60 diamidino-2-phenylindole (DAPI). Cells were analyzed by fluorescence microscopy (Leica DMI6000 B, Leica Microsystems; software: Leica Application Suite) 48 h post transfection.

The microscopy pictures show strong fluorescein fluorescence in the cytosol of cells treated with oligonucleotides containing tc$^{hd}$T (subscript e of example 6) (SEQ ID NO:18), while no fluorescence is observed when oligonucleotides containing tc$^{ee}$T (subscript b of example 6) (SEQ ID NO:17) or tcT (subscript a of example 6) (SEQ ID NO:19) were used.

What is claimed is:

1. A tricyclic nucleoside described by general Formula I:

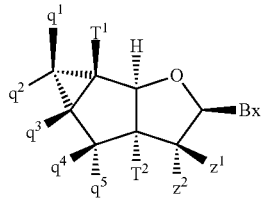

wherein:

Bx is a heterocyclic base moiety;

one of $T^1$ and $T^2$ is hydroxyl (—OH) or a protected hydroxyl and the other of $T^1$ and $T^2$ is a phosphate or a reactive phosphorus group;

$q^1$ and $q^2$ are each, independently, H, F or Cl, at least one of $q^3$, $q^4$ and $q^5$ is, independently, a group described by a general formula $-A^1-X_h-A^2-Y_n$, wherein $A^1$ is a $C_k$-alkyl, $C_k$-alkenyl or $C_k$-alkynyl, with k being an integer selected from the range of 0 to 20, $X_h$ is —C(=O)—, —C(=O)NR—, —O—, —S—, —NR—, —C(=O)R, —C(=O)OR, —C(=O)NR$_2$—, —OR, —SR or —NR$_2$, with each R being selected independently from H, methyl, ethyl, propyl, butyl, acetyl and 2-hydroxyethyl, and h is 0 or 1, $A^2$ is a $C_i$-alkyl, $C_i$-alkenyl or $C_i$-alkynyl, with i being an integer selected from the range of 0 to 20, Y is a substituent group attached to any carbon atom on $A^1$ and/or $A^2$, selected from —F, —Cl, —Br, =O, —OR, —SR, —NR$_2$, —NR$_3^+$, NHC(=NH)NH$_2$, —CN, —NC, —NCO, —NCS, —SCN, —COR, —CO$_2$R, CONR$_2$, —R, with each R being selected independently from H, methyl, ethyl, propyl, butyl, acetyl and 2-hydroxyethyl, and n is 0, 1, 2, 3, 4, 5 or 6, wherein k+i equals at least 1, the other ones of $q^3$, $q^4$ and $q^5$ are, independently, H, F or Cl, one of $z^1$ and $z^2$ is H and the other of $z^1$ and $z^2$ is H, —OH, F, Cl, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$ or OCH$_2$—N(H)—C(=NH)NH$_2$.

2. The tricyclic nucleoside of claim 1, wherein Bx is uracil, thymine, cytosine, 5-methylcytosine, adenine or guanine.

3. The tricyclic nucleoside of claim 1, wherein $T^1$ is hydroxyl or protected hydroxyl, and wherein $T^2$ is a reactive phosphorus group selected from an H-phosphonate or a phosphoramidite.

4. The tricyclic nucleoside of claim 1, wherein $T^1$ is 4,4'-dimethoxytrityl and $T^2$ is diisopropylcyanoethoxy phosphoramidite or a controlled pore glass surface.

5. The tricyclic nucleoside of claim 1, wherein $q^3$ is described by the general formula $-A^1X_h-A^2-Y_n$, and $q^4$ and $q^5$, independently of each other, are H, F or Cl.

6. The tricyclic nucleoside of claim 1, wherein k is an integer from 3 to 16, h is 0, i is 0 and n is 1, 2, or 3.

7. The tricyclic nucleoside of claim 1, wherein k is 1, h is 1 and X is —O—, COO—, CONH— or CONR—, i is an integer from 3 to 16 and n is 1, 2, or 3.

8. The tricyclic nucleoside of claim 1, wherein n is 1 and Y is selected from NH$_2$, NHR, NR$_2$, NR$_3^+$ and NHC(=NH) NH$_2$, with R having the meaning defined above.

9. The tricyclic nucleoside of claim 1, wherein Y is in the ω-position.

10. The tricyclic nucleoside of claim 1, wherein the sum of i+k is an integer from 3 to 16, particularly from 3 to 12, more particularly from 5 to 10.

11. The tricycle nucleoside of claim 1, wherein $A^1$ is CH$_2$, h is 1 and $X_h$ is —C(=O)O—, —C(=O)NH—, and $A^2$ is a C2 to C16 alkyl, $Y_n$, is NH$_2$ and n is 0 or 1.

12. The tricyclic nucleoside of claim 1, wherein $A^1$ is CH$_2$.

13. The tricycle nucleoside of claim 1, wherein k is 0.

14. A tricyclic nucleoside selected from the group of a.

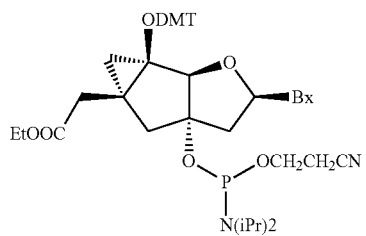

b.

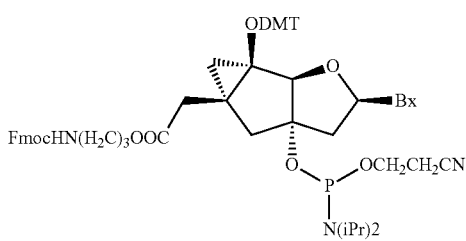

c.

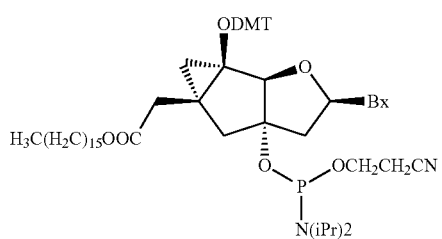

d.

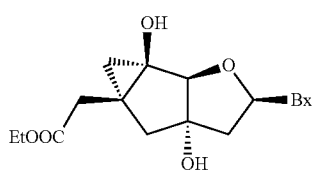

e.

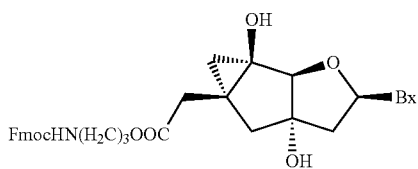

f.

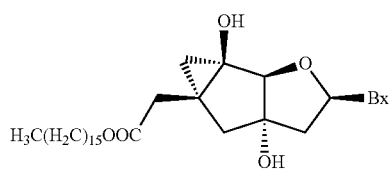

wherein Bx is selected from uracil, thymine, cytosine, 5-methylcytosine, adenine and guanine.

15. An oligomeric compound comprising at least one tricyclic nucleoside according to claim 1, wherein said oligomeric compound comprises from 8 to 40 monomeric subunits.

16. The oligomeric compound of claim 15, wherein each Bx is, independently, uracil, thymine, cytosine, 5-methylcytosine, adenine or guanine.

17. The oligomeric compound of claim 15, wherein each internucleoside linking group is, independently, a phosphodiester internucleoside linking group or a phosphorothioate internucleoside linking group.

18. The oligomeric compound of claim 15, comprising a first region having at least two contiguous tricyclic nucleosides having Formula II.

19. The oligomeric compound of claim 18 comprising a second region having at least two contiguous monomeric subunits wherein each monomeric subunit in the second region is a modified nucleoside different from the tricyclic nucleosides of Formula II of said first region.

20. The oligomeric compound of claim 19 further comprising a third region located between said first and second regions wherein each monomer subunit in the third region is independently, a nucleoside or a modified nucleoside that is different from each tricyclic nucleoside of Formula II of the first region and each monomer subunit of the second region.

21. The oligomeric compound of claim 15 comprising a gapped oligomeric compound having an internal region of from 6 to 14 contiguous monomer subunits flanked on each side by an external region of from 1 to 5 contiguous monomer subunits wherein each monomer subunit in each external region is a tricyclic nucleoside of Formula II and each monomer subunit in the internal region is, independently, a nucleoside or a modified nucleoside.

22. The oligomeric compound of of claim 15, comprising one or several nucleotide blocks selected from a.

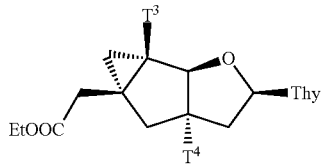

b.

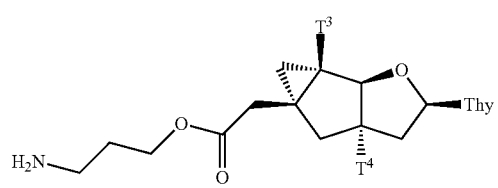

c.

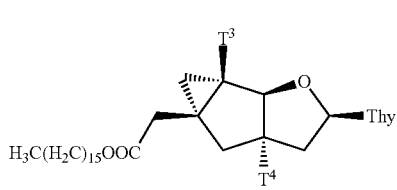

wherein $T^3$ and $T^4$ have the meanings outlined above.

23. A method for solid-phase synthesis of an oligonucleotide comprising the use of a tricyclic nucleoside according to claim 1.

* * * * *

UNITED STATES PATENT AND TRADEMARK OFFICE
CERTIFICATE OF CORRECTION

PATENT NO. : 9,249,178 B2
APPLICATION NO. : 14/385050
DATED : February 2, 2016
INVENTOR(S) : Christian Leumann et al.

It is certified that error appears in the above-identified patent and that said Letters Patent is hereby corrected as shown below:

In the Claims

Col. 55, line 42 (Claim 1): "Xh is -C(=O)-, -C(=O)NR-, -O-, -S-" should be
-- Xh is -C(=O)-, -C(=O)O-, -C(=O)NR-, -O-, -S- --

Signed and Sealed this
Thirty-first Day of May, 2016

Michelle K. Lee
*Director of the United States Patent and Trademark Office*

SEQUENCE LISTING

<160> NUMBER OF SEQ ID NOS: 20

<210> SEQ ID NO 1
<211> LENGTH: 10
<212> TYPE: DNA
<213> ORGANISM: Artificial Sequence
<220> FEATURE:
<223> OTHER INFORMATION: Sequence for biophysical analysis

<400> SEQUENCE: 1
aactgtcacg                                                          10

<210> SEQ ID NO 2
<211> LENGTH: 10
<212> TYPE: DNA
<213> ORGANISM: Artificial Sequence
<220> FEATURE:
<223> OTHER INFORMATION: Synthetic oligomer with modified nucleoside
      according to Example 6
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid ethylester substitution in
      position q3

<400> SEQUENCE: 2 aactgncacg                                                          10

<210> SEQ ID NO 3
<211> LENGTH: 10
<212> TYPE: DNA
<213> ORGANISM: Artificial Sequence
<220> FEATURE:
<223> OTHER INFORMATION: Synthetic oligomer with modified nucleoside
      according to Example 6
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid moiety in position q3

<400> SEQUENCE: 3 aactgncacg                                                          10

<210> SEQ ID NO 4
<211> LENGTH: 10
<212> TYPE: DNA
<213> ORGANISM: Artificial Sequence
<220> FEATURE:
<223> OTHER INFORMATION: Synthetic oligomer with modified nucleoside
      according to Example 6
<220> FEATURE:
<221> NAME/KEY: misc_feature
<222> LOCATION: (4)..(4)

```
<223> OTHER INFORMATION: n at position 4 is t, with a tricyclic
      nucleoside having ethanoic acid ethylester substitution in
      position q3

<400> SEQUENCE: 4 aacngtcacg                                                              10

<210> SEQ ID NO 5
<211> LENGTH: 10
<212> TYPE: DNA
<213> ORGANISM: Artificial Sequence
<220> FEATURE:
<223> OTHER INFORMATION: Synthetic oligomer with modified nucleoside
      according to Example 6
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid moiety in position q3

<400> SEQUENCE: 5 aacngtcacg                                                              10

<210> SEQ ID NO 6
<211> LENGTH: 10
<212> TYPE: DNA
<213> ORGANISM: Artificial Sequence
<220> FEATURE:
<223> OTHER INFORMATION: Synthetic oligomer with modified nucleosides
      according to Example 6
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid ethylester substitution in
      position q3
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid ethylester substitution in
      position q3

<400> SEQUENCE: 6 aacngncacg                                                              10

<210> SEQ ID NO 7
<211> LENGTH: 10
<212> TYPE: DNA
<213> ORGANISM: Artificial Sequence
<220> FEATURE:
<223> OTHER INFORMATION: Synthetic oligomer with modified nucleosides
      according to Example 6
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid amide substitution in position
      q3
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid amide substitution in position
      q3

<400> SEQUENCE: 7 aacngncacg                                                              10

<210> SEQ ID NO 8
<211> LENGTH: 10
```

```
<212> TYPE: DNA
<213> ORGANISM: Artificial Sequence
<220> FEATURE:
<223> OTHER INFORMATION: Synthetic oligomer with modified nucleosides
      according to Example 6
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid substitution in position q3
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid substitution in position q3

<400> SEQUENCE: 8 aacngncacg                                                          10

<210> SEQ ID NO 9
<211> LENGTH: 10
<212> TYPE: DNA
<213> ORGANISM: Artificial Sequence
<220> FEATURE:
<223> OTHER INFORMATION: Synthetic oligomer with modified nucleosides
      according to Example 6
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid hexadecylester substitution in
      position q3
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid hexadecylester substitution in
      position q3

<400> SEQUENCE: 9 aacngncacg                                                          10

<210> SEQ ID NO 10
<211> LENGTH: 10
<212> TYPE: DNA
<213> ORGANISM: Artificial Sequence
<220> FEATURE:
<223> OTHER INFORMATION: Synthetic oligomer with modified nucleosides
      according to Example 6
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid hydroxypropylamide substitution
      in position q3
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid hydroxypropylamide substitution
      in position q3

<400> SEQUENCE: 10 aacngncacg                                                          10

<210> SEQ ID NO 11
<211> LENGTH: 10
<212> TYPE: DNA
<213> ORGANISM: Artificial Sequence
<220> FEATURE:
<223> OTHER INFORMATION: Synthetic oligomer for biophysical analysis
<220> FEATURE:
<221> NAME/KEY: misc_feature
```

-continued

```
<222> LOCATION: (1)..(2)
<223> OTHER INFORMATION: n at positions 1 and 2 is a, with a tricyclic
      nucleoside without substituents
<220> FEATURE:
<221> NAME/KEY: misc_feature
<222> LOCATION: (3)..(3)
<223> OTHER INFORMATION: n at position 3 is c, with a tricyclic
      nucleoside without substituents
<220> FEATURE:
<221> NAME/KEY: misc_feature
<222> LOCATION: (4)..(4)
<223> OTHER INFORMATION: n at position 4 is t, with a tricyclic
      nucleoside without substituents
<220> FEATURE:
<221> NAME/KEY: misc_feature
<222> LOCATION: (5)..(5)
<223> OTHER INFORMATION: n at position 5 is g, with a tricyclic
      nucleoside without substituents
<220> FEATURE:
<221> NAME/KEY: misc_feature
<222> LOCATION: (6)..(6)
<223> OTHER INFORMATION: n at position 6 is t, with a tricyclic
      nucleoside without substituents
<220> FEATURE:
<221> NAME/KEY: misc_feature
<222> LOCATION: (7)..(7)
<223> OTHER INFORMATION: n at position 7 is c, with a tricyclic
      nucleoside without substituents
<220> FEATURE:
<221> NAME/KEY: misc_feature
<222> LOCATION: (8)..(8)
<223> OTHER INFORMATION: n at position 8 is a, with a tricyclic
      nucleoside without substituents
<220> FEATURE:
<221> NAME/KEY: misc_feature
<222> LOCATION: (9)..(9)
<223> OTHER INFORMATION: n at position 9 is c, with a tricyclic
      nucleoside without substituents
<220> FEATURE:
<221> NAME/KEY: misc_feature
<222> LOCATION: (10)..(10)
<223> OTHER INFORMATION: n at position 10 is g, with a tricyclic
      nucleoside without substituents

<400> SEQUENCE: 11 nnnnnnnnnn                                                          10

<210> SEQ ID NO 12
<211> LENGTH: 10
<212> TYPE: DNA
<213> ORGANISM: Artificial Sequence
<220> FEATURE:
<223> OTHER INFORMATION: Synthetic oligomer for biophysical analysis
<220> FEATURE:
<221> NAME/KEY: misc_feature
<222> LOCATION: (1)..(2)
<223> OTHER INFORMATION: n at positions 1 and 2 is a, with a tricyclic
      nucleoside without substituents
<220> FEATURE:
<221> NAME/KEY: misc_feature
<222> LOCATION: (3)..(3)
<223> OTHER INFORMATION: n at position 3 is c, with a tricyclic
      nucleoside without substituents
<220> FEATURE:
<221> NAME/KEY: misc_feature
<222> LOCATION: (4)..(4)
<223> OTHER INFORMATION: n at position 4 is t, with a tricyclic
      nucleoside without substituents
<220> FEATURE:
<221> NAME/KEY: misc_feature
<222> LOCATION: (5)..(5)
<223> OTHER INFORMATION: n at position 5 is g, with a tricyclic
      nucleoside without substituents
<220> FEATURE:
<221> NAME/KEY: misc_feature
<222> LOCATION: (6)..(6)
<223> OTHER INFORMATION: n at position 6 is t, with a tricyclic
```

```
    nucleoside with an ethanoic acid substitution in q3
<220> FEATURE:
<221> NAME/KEY: misc_feature
<222> LOCATION: (7)..(7)
<223> OTHER INFORMATION: n at position 7 is c, with a tricyclic
      nucleoside without substituents
<220> FEATURE:
<221> NAME/KEY: misc_feature
<222> LOCATION: (8)..(8)
<223> OTHER INFORMATION: n at position 8 is a, with a tricyclic
      nucleoside without substituents
<220> FEATURE:
<221> NAME/KEY: misc_feature
<222> LOCATION: (9)..(9)
<223> OTHER INFORMATION: n at position 9 is c, with a tricyclic
      nucleoside without substituents
<220> FEATURE:
<221> NAME/KEY: misc_feature
<222> LOCATION: (10)..(10)
<223> OTHER INFORMATION: n at position 10 is g, with a tricyclic
      nucleoside without substituents

<400> SEQUENCE: 12 nnnnnnnnnn                                                           10

<210> SEQ ID NO 13
<211> LENGTH: 10
<212> TYPE: DNA
<213> ORGANISM: Artificial Sequence
<220> FEATURE:
<223> OTHER INFORMATION: Synthetic oligomer for biophysical analysis
<220> FEATURE:
<221> NAME/KEY: misc_feature
<222> LOCATION: (1)..(2)
<223> OTHER INFORMATION: n at positions 1 and 2 is a, with a tricyclic
      nucleoside without substituents
<220> FEATURE:
<221> NAME/KEY: misc_feature
<222> LOCATION: (3)..(3)
<223> OTHER INFORMATION: n at position 3 is c, with a tricyclic
      nucleoside without substituents
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid substitution in position q3
<220> FEATURE:
<221> NAME/KEY: misc_feature
<222> LOCATION: (5)..(5)
<223> OTHER INFORMATION: n at position 5 is g, with a tricyclic
      nucleoside without substituents
<220> FEATURE:
<221> NAME/KEY: misc_feature
<222> LOCATION: (6)..(6)
<223> OTHER INFORMATION: n at position 6 is t, with a tricyclic
      nucleoside without substituents
<220> FEATURE:
<221> NAME/KEY: misc_feature
<222> LOCATION: (7)..(7)
<223> OTHER INFORMATION: n at position 7 is c, with a tricyclic
      nucleoside without substituents
<220> FEATURE:
<221> NAME/KEY: misc_feature
<222> LOCATION: (8)..(8)
<223> OTHER INFORMATION: n at position 8 is a, with a tricyclic
      nucleoside without substituents
<220> FEATURE:
<221> NAME/KEY: misc_feature
<222> LOCATION: (9)..(9)
<223> OTHER INFORMATION: n at position 9 is c, with a tricyclic
      nucleoside without substituents
<220> FEATURE:
<221> NAME/KEY: misc_feature
<222> LOCATION: (10)..(10)
<223> OTHER INFORMATION: n at position 10 is g, with a tricyclic
      nucleoside without substituents
```

-continued

<400> SEQUENCE: 13 nnnnnnnnnn                                                            10

<210> SEQ ID NO 14
<211> LENGTH: 10
<212> TYPE: DNA
<213> ORGANISM: Artificial Sequence
<220> FEATURE:
<223> OTHER INFORMATION: Synthetic oligomer for biophysical analysis
<220> FEATURE:
<221> NAME/KEY: misc_feature
<222> LOCATION: (1)..(2)
<223> OTHER INFORMATION: n at positions 1 and 2 is a, with a tricyclic
      nucleoside without substituents
<220> FEATURE:
<221> NAME/KEY: misc_feature
<222> LOCATION: (3)..(3)
<223> OTHER INFORMATION: n at position 3 is c, with a tricyclic
      nucleoside without substituents
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid ethylester substitution in
      position q3
<220> FEATURE:
<221> NAME/KEY: misc_feature
<222> LOCATION: (5)..(5)
<223> OTHER INFORMATION: n at position 5 is g, with a tricyclic
      nucleoside without substituents
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid ethylester substitution in
      position q3
<220> FEATURE:
<221> NAME/KEY: misc_feature
<222> LOCATION: (7)..(7)
<223> OTHER INFORMATION: n at position 7 is c, with a tricyclic
      nucleoside without substituents
<220> FEATURE:
<221> NAME/KEY: misc_feature
<222> LOCATION: (8)..(8)
<223> OTHER INFORMATION: n at position 8 is a, with a tricyclic
      nucleoside without substituents
<220> FEATURE:
<221> NAME/KEY: misc_feature
<222> LOCATION: (9)..(9)
<223> OTHER INFORMATION: n at position 9 is c, with a tricyclic
      nucleoside without substituents
<220> FEATURE:
<221> NAME/KEY: misc_feature
<222> LOCATION: (10)..(10)
<223> OTHER INFORMATION: n at position 10 is g, with a tricyclic
      nucleoside without substituents

<400> SEQUENCE: 14 nnnnnnnnnn                                                            10

<210> SEQ ID NO 15
<211> LENGTH: 10
<212> TYPE: DNA
<213> ORGANISM: Artificial Sequence
<220> FEATURE:
<223> OTHER INFORMATION: Synthetic oligomer for biophysical analysis
<220> FEATURE:
<221> NAME/KEY: misc_feature
<222> LOCATION: (1)..(2)
<223> OTHER INFORMATION: n at positions 1 and 2 is a, with a tricyclic
      nucleoside without substituents
<220> FEATURE:
<221> NAME/KEY: misc_feature
<222> LOCATION: (3)..(3)
<223> OTHER INFORMATION: n at position 3 is c, with a tricyclic

```
                            nucleoside without substituents
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid amide substitution in position
      q3
<220> FEATURE:
<221> NAME/KEY: misc_feature
<222> LOCATION: (5)..(5)
<223> OTHER INFORMATION: n at position 5 is g, with a tricyclic
      nucleoside without substituents
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid amide substitution in position
      q3
<220> FEATURE:
<221> NAME/KEY: misc_feature
<222> LOCATION: (7)..(7)
<223> OTHER INFORMATION: n at position 7 is c, with a tricyclic
      nucleoside without substituents
<220> FEATURE:
<221> NAME/KEY: misc_feature
<222> LOCATION: (8)..(8)
<223> OTHER INFORMATION: n at position 8 is a, with a tricyclic
      nucleoside without substituents
<220> FEATURE:
<221> NAME/KEY: misc_feature
<222> LOCATION: (9)..(9)
<223> OTHER INFORMATION: n at position 9 is c, with a tricyclic
      nucleoside without substituents
<220> FEATURE:
<221> NAME/KEY: misc_feature
<222> LOCATION: (10)..(10)
<223> OTHER INFORMATION: n at position 10 is g, with a tricyclic
      nucleoside without substituents

<400> SEQUENCE: 15 nnnnnnnnnn                                                            10

<210> SEQ ID NO 16
<211> LENGTH: 10
<212> TYPE: DNA
<213> ORGANISM: Artificial Sequence
<220> FEATURE:
<223> OTHER INFORMATION: Synthetic oligomer for biophysical analysis
<220> FEATURE:
<221> NAME/KEY: misc_feature
<222> LOCATION: (1)..(2)
<223> OTHER INFORMATION: n at positions 1 and 2 is a, with a tricyclic
      nucleoside without substituents
<220> FEATURE:
<221> NAME/KEY: misc_feature
<222> LOCATION: (3)..(3)
<223> OTHER INFORMATION: n at position 3 is c, with a tricyclic
      nucleoside without substituents
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid substitution in position q3
<220> FEATURE:
<221> NAME/KEY: misc_feature
<222> LOCATION: (5)..(5)
<223> OTHER INFORMATION: n at position 5 is g, with a tricyclic
      nucleoside without substituents
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid substitution in position q3
<220> FEATURE:
<221> NAME/KEY: misc_feature
<222> LOCATION: (7)..(7)
<223> OTHER INFORMATION: n at position 7 is c, with a tricyclic
``` nucleoside without substituents
<220> FEATURE:
<221> NAME/KEY: misc_feature
<222> LOCATION: (8)..(8)
<223> OTHER INFORMATION: n at position 8 is a, with a tricyclic
    nucleoside without substituents
<220> FEATURE:
<221> NAME/KEY: misc_feature
<222> LOCATION: (9)..(9)
<223> OTHER INFORMATION: n at position 9 is c, with a tricyclic
    nucleoside without substituents
<220> FEATURE:
<221> NAME/KEY: misc_feature
<222> LOCATION: (10)..(10)
<223> OTHER INFORMATION: n at position 10 is g, with a tricyclic
    nucleoside without substituents

<400> SEQUENCE: 16 nnnnnnnnnn                                                             10

<210> SEQ ID NO 17
<211> LENGTH: 10
<212> TYPE: DNA
<213> ORGANISM: Artificial Sequence
<220> FEATURE:
<223> OTHER INFORMATION: Synthetic oligomer for biophysical analysis
<220> FEATURE:
<221> NAME/KEY: misc_feature
<222> LOCATION: (2)..(2)
<223> OTHER INFORMATION: n at position 2 is t, with a tricyclic
    nucleoside having ethanoic acid ethylester substitution in
    position q3
<220> FEATURE:
<221> NAME/KEY: misc_feature
<222> LOCATION: (4)..(4)
<223> OTHER INFORMATION: n at position 4 is t, with a tricyclic
    nucleoside having ethanoic acid ethylester substitution in
    position q3
<220> FEATURE:
<221> NAME/KEY: misc_feature
<222> LOCATION: (6)..(6)
<223> OTHER INFORMATION: n at position 6 is t, with a tricyclic
    nucleoside having ethanoic acid ethylester substitution in
    position q3
<220> FEATURE:
<221> NAME/KEY: misc_feature
<222> LOCATION: (8)..(8)
<223> OTHER INFORMATION: n at position 8 is t, with a tricyclic
    nucleoside having ethanoic acid ethylester substitution in
    position q3
<220> FEATURE:
<221> NAME/KEY: misc_feature
<222> LOCATION: (10)..(10)
<223> OTHER INFORMATION: n at position 10 is t, with a tricyclic
    nucleoside having ethanoic acid ethylester substitution in
    position q3
<220> FEATURE:
<221> NAME/KEY: misc_feature
<222> LOCATION: (10)..(10)
<223> OTHER INFORMATION: n at position 10 is modified with a
    6-carboxyfluorescein moiety

<400> SEQUENCE: 17 tntntntntn                                                             10

<210> SEQ ID NO 18
<211> LENGTH: 10
<212> TYPE: DNA
<213> ORGANISM: Artificial Sequence
<220> FEATURE:
<223> OTHER INFORMATION: Synthetic oligomer for biophysical analysis
<220> FEATURE:
<221> NAME/KEY: misc_feature
<222> LOCATION: (2)..(2)
<223> OTHER INFORMATION: n at position 2 is t, with a tricyclic

```
      nucleoside having an ethanoic acid hexadecylester substitution in
      position q3
<220> FEATURE:
<221> NAME/KEY: misc_feature
<222> LOCATION: (4)..(4)
<223> OTHER INFORMATION: n at position 4 is t, with a tricyclic
      nucleoside having an ethanoic acid hexadecylester substitution in
      position q3
<220> FEATURE:
<221> NAME/KEY: misc_feature
<222> LOCATION: (6)..(6)
<223> OTHER INFORMATION: n at position 6 is t, with a tricyclic
      nucleoside having an ethanoic acid hexadecylester substitution in
      position q3
<220> FEATURE:
<221> NAME/KEY: misc_feature
<222> LOCATION: (8)..(8)
<223> OTHER INFORMATION: n at position 8 is t, with a tricyclic
      nucleoside having an ethanoic acid hexadecylester substitution in
      position q3
<220> FEATURE:
<221> NAME/KEY: misc_feature
<222> LOCATION: (10)..(10)
<223> OTHER INFORMATION: n at position 10 is t, with a tricyclic
      nucleoside having an ethanoic acid hexadecylester substitution in
      position q3
<220> FEATURE:
<221> NAME/KEY: misc_feature
<222> LOCATION: (10)..(10)
<223> OTHER INFORMATION: n at position 10 is modified with a
      6-carboxyfluorescein moiety

<400> SEQUENCE: 18 tntntntntn                                                        10

<210> SEQ ID NO 19
<211> LENGTH: 10
<212> TYPE: DNA
<213> ORGANISM: Artificial Sequence
<220> FEATURE:
<223> OTHER INFORMATION: Synthetic oligomer for biophysical analysis
<220> FEATURE:
<221> NAME/KEY: misc_feature
<222> LOCATION: (2)..(2)
<223> OTHER INFORMATION: n at position 2 is t, with a tricyclic
      nucleoside without substituents
<220> FEATURE:
<221> NAME/KEY: misc_feature
<222> LOCATION: (4)..(4)
<223> OTHER INFORMATION: n at position 4 is t, with a tricyclic
      nucleoside without substituents
<220> FEATURE:
<221> NAME/KEY: misc_feature
<222> LOCATION: (6)..(6)
<223> OTHER INFORMATION: n at position 6 is t, with a tricyclic
      nucleoside without substituents
<220> FEATURE:
<221> NAME/KEY: misc_feature
<222> LOCATION: (8)..(8)
<223> OTHER INFORMATION: n at position 8 is t, with a tricyclic
      nucleoside without substituents
<220> FEATURE:
<221> NAME/KEY: misc_feature
<222> LOCATION: (10)..(10)
<223> OTHER INFORMATION: n at position 10 is t, with a tricyclic
      nucleoside without substituents
<220> FEATURE:
<221> NAME/KEY: misc_feature
<222> LOCATION: (10)..(10)
<223> OTHER INFORMATION: n at position 10 is modified with a
      6-carboxyfluorescein moiety

<400> SEQUENCE: 19 tntntntntn                                                        10
```

```
<210> SEQ ID NO 20
<211> LENGTH: 10
<212> TYPE: DNA
<213> ORGANISM: Artificial Sequence
<220> FEATURE:
<223> OTHER INFORMATION: Synthetic oligomer for biophysical analysis
<220> FEATURE:
<221> NAME/KEY: misc_feature
<222> LOCATION: (10)..(10)
<223> OTHER INFORMATION: t at position 10 is modified with a
      6-carboxyfluorescein moiety

<400> SEQUENCE: 20
tttttttttt                                                           10
```